US012797554B2

(12) United States Patent
Kast et al.

(10) Patent No.: US 12,797,554 B2
(45) Date of Patent: Nov. 17, 2026

(54) MANUAL SAFETY INJECTOR FOR 5-10 ML FLUID DELIVERY

(71) Applicant: Becton, Dickinson and Company, Franklin Lakes, NJ (US)

(72) Inventors: Nathan Kast, Fort Lauderdale, FL (US); Slobodan Stefanov, Deerfield Beach, FL (US); Michael Vincent Quinn, East Hanover, NJ (US); Richard A Cronenberg, Mahwah, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 331 days.

(21) Appl. No.: 18/731,787

(22) Filed: Jun. 3, 2024

(65) Prior Publication Data

US 2025/0367387 A1 Dec. 4, 2025

(51) Int. Cl.
*A61M 5/315* (2006.01)
*A61M 5/32* (2006.01)

(52) U.S. Cl.
CPC .... *A61M 5/31591* (2013.01); *A61M 5/31511* (2013.01); *A61M 5/3202* (2013.01)

(58) Field of Classification Search
CPC .......... A61M 5/31591; A61M 5/31511; A61M 5/3202; A61M 5/2429; A61M 2005/2407; A61M 2005/2433; A61M 2005/247; A61M 2005/2485; A61M 5/24; A61M 5/3158; A61M 2005/3267; A61M 2205/273; A61M 2205/583; A61M 2205/8281; A61M 5/31505; A61M 5/3234; A61M 5/326; A61M 5/3271; A61M 5/46; A61M 5/502; A61M 2005/312; A61M 2005/31508
See application file for complete search history.

(56) References Cited

U.S. PATENT DOCUMENTS 11,547,808 B2* 1/2023 Kramer .................. A61M 5/19
2012/0022466 A1 1/2012 James et al.
2016/0193414 A1 7/2016 McLoughlin et al.
2017/0157332 A1* 6/2017 Nguyen .............. A61M 5/3204
2020/0139048 A1* 5/2020 Buchine ................ A61M 5/284

FOREIGN PATENT DOCUMENTS

GB 2617389 A 10/2023
WO 2015081337 A2 6/2015

* cited by examiner

*Primary Examiner* — Amal Aly Farag
(74) *Attorney, Agent, or Firm* — The Webb Law Firm

(57) ABSTRACT

Provided herein is a manual safety injector that includes a container assembly, an injector assembly and a plunger assembly. The container assembly includes a container pre-filled with 5 to 10 mL of fluid therein and a needle assembly comprising a double-ended needle. The injector assembly includes an inner container holder, a middle body, and an outer holder in a nested arrangement, with the inner container holder movable within the middle body and the middle body movable within the outer holder. A first actuation of the plunger assembly moves the inner container holder distally within the middle body, to extend a distal end of the needle, and moves the needle assembly to place the needle in fluid communication with the container. An additional actuation of the plunger assembly expels fluid from the container and actuates a biasing member in the injector assembly to retract the needle back into the outer holder.

22 Claims, 34 Drawing Sheets

MANUAL SAFETY INJECTOR FOR 5-10 ML FLUID DELIVERY

BACKGROUND OF THE INVENTION

Field of the Invention

The present disclosure relates generally to drug delivery devices and, more specifically, to manual safety injectors that provide for the self-administering injection of a dose of medicament between 5 and 10 mL.

Description of Related Art

Syringes and other injection devices are used in a variety of environments for administering fluids to a patient. When used in controlled healthcare environments and by trained healthcare professionals, such devices provide an effective and cost-efficient solution for the administering of vaccines or other medicaments to a patient. However, it is recognized that it is often desirable for perform the injection of vaccines or other medicaments to a patient in the home or in another environment outside of a healthcare facility.

One solution for performing an injection in the home is via an automated drug delivery device worn by the patient, i.e., an auto-injection device or "auto-injector." Wearable auto-injectors may be pre-programmed or otherwise controlled to deliver a measured dose of medication/drug to a patient at a specified rate and/or time. Auto-injectors may be designed as single use devices that are disposed after use or as reusable injectors that allow a user to load and unload a standard pre-filled syringe thereto. While such wearable auto-injectors are effective and reliable for performing injections, it is recognized that such devices are complicated devices that are costly to manufacture and may also be cumbersome for a user to wear over a prolonged period.

Another solution for performing an injection in the home is to utilize a manual injector. With such manual injectors, it is often necessary for a nurse or other healthcare professional to handle the injector and perform the manual injection, which may be inconvenient for the patient (as compared to self-delivery/injection) and/or increase the overall cost of care. For manual injection devices that incorporate safety and/or delivery features therein so as to enable a patient to self-inject at home, the range of products available is limited—with existing manual injection devices of this type only being available for injectors in the range of 1-3 mL in volume. Additionally, existing manual injection devices may require the user to follow a sequence of steps to enable the injection-including the performing of an initial assembly/loading of the injection device, etc-which can make use of the injector more complicated and increase the possibility of user error.

Accordingly, a need exists in the art for a manual safety injector that is useable by a patient to self-inject a higher volume of medicament, such as 5-10 mL. The manual safety injector may be provided to the patient pre-assembled, so as to reduce initial assembly and/or loading steps for the device. The manual safety injector may include features therein that simplify the injection process, such as by the injector adhering to the skin of the patient. The manual safety injector may also include features therein that automatically cover a needle after use and that enable the patient to deliver the medicament at a desired speed.

SUMMARY OF THE INVENTION

Provided herein is a manual safety injector that includes a container assembly comprising a container pre-filled with 5 to 10 mL of fluid therein, with a stopper positioned in the container at a proximal end thereof and a septum positioned in the container at a distal end thereof, to seal the fluid in the container, and a needle assembly comprising a double-ended needle having a sharp proximal end and a sharp distal end. The manual safety injector also includes an injector assembly comprising an inner container holder within which the container is retained, a middle body positioned about the inner container holder, with the inner container holder movable within the middle body in a longitudinal direction, an outer holder positioned about the middle body, with the middle body movable within the outer holder in a longitudinal direction, and a biasing member positioned between the middle body and the outer holder, at a distal end of each of the middle body and the outer holder. The manual safety injector further includes a plunger assembly engageable with the injector assembly and the container assembly, with the plunger assebmly including a plunger rod or shaft configured to advance the stopper within the container to expel fluid out from the container. A first actuation of the plunger assembly causes the inner container holder to move distally within the middle body, to extend the sharp distal end of the needle out distally past the outer holder for insertion of the needle into a patient, and causes the needle assembly to move from a first position where the sharp proximal end is separated from the septum to a second position where the sharp proximal end is positioned to pierce through the septum, to place the needle in fluid communication with the fluid within the container. An additional actuation of the plunger assembly causes the fluid to be expelled out from the container and causes the middle body to release from the outer holder, such that the biasing member is able to actuate and move the container assembly, the inner container holder, and the middle body distally within the outer holder, to retract the sharp distal end of the needle back into the outer holder.

In some embodiments, the manual safety injector further includes a cap assembly positioned at the distal end of the container, the cap assembly comprising a protective cap engaged to a port of the container, at the distal end of the container; and a tip cap needle holder engaged with the protective cap, the tip cap needle holder including an annular seat configured to receive a portion of the needle assembly.

In some embodiments, the needle assembly comprises a hub comprising a distal end, a proximal end, with a hole extending between the distal and proximal ends of the hub that retains the needle therein, and wherein the proximal end of the hub is seated within the annular seat of the tip cap needle holder and is seated therein.

In some embodiments, the hub moves proximally into the annular seat upon application of a sufficient force against the hub, thereby moving the needle assembly from the first position to the second position, so that the sharp proximal end pierces through the septum, to place the needle in fluid communication with the fluid within the container.

In some embodiments, the needle assembly comprises a needle cap coupled to the distal end of the hub, so as to be positioned over the sharp distal end of the needle.

In some embodiments, the outer holder comprises a foot at the distal end thereof that substantially closes the distal end of the outer holder, the foot comprising a flat distal-facing surface configured for placement against the skin of a patient during use of the manual safety injector.

In some embodiments, the distal-facing surface of the foot comprises an adhesive patch that covers a portion or all of the distal-facing surface.

In some embodiments, the injector assembly further comprises a safety cap affixed to the distal-facing surface of the foot, the safety cap comprising a cover applied over the distal-facing surface of the foot, the cover including a needle opening therein, a pull tab extending over distally from the cover and including a grip configured to be pulled by a user, and a loop connecting the pull tab and the cover, so that a pulling force applied to the grip is transferred to the cover, to enable removal of the safety cap from the foot.

In some embodiments, the safety cap comprises a receptacle therein extending proximally through the cover, the receptacle configured to receive and retain the needle cap therein, such that removal of the safety cap from the foot also causes removal of the needle cap.

In some embodiments, the middle body comprises a proximal end member including a flanged portion having a pair of openings formed therein, and wherein the outer holder comprises a pair of hook members formed at a proximal end thereof and that extend out in a proximal direction through the pair of openings to engage the proximal end member.

In some embodiments, the plunger assembly comprises a plunger rod and a thumb press at a proximal end of the plunger rod and a plunger retainer positioned on the plunger rod, with an opening formed through the plunger retainer through which the plunger rod extends, the plunger retainer configured to engage the inner container holder.

In some embodiments, the additional actuation of the plunger assembly causes the thumb press to push distally against the pair of hook members and cause the pair of hook members to disengage from the proximal end member and slide distally through the pair of openings, thereby releasing the middle body from the outer holder.

In some embodiments, the plunger assembly comprises an outer grip having a closed proximal end and an open distal end, with an inner surface of the outer grip defining a hollow inner chamber, and a plunger shaft connected to the inner surface at the closed proximal end and extending distally therefrom, the plunger shaft configured to engage the stopper and advance the stopper distally within the container.

In some embodiments, the outer grip comprises a pair of longitudinally oriented rails formed on opposing sides of the inner surface the pair or rails configured to interact with the middle body and outer holder, to provide for a distal advancement of the plunger assembly.

In some embodiments, the middle body further comprises a pair of release tabs configured to selectively engage the outer holder to retain the middle body in-place within the outer holder, and wherein the additional actuation of the plunger assembly causes the pair of rails to deflect the pair of release tabs, thereby releasing the middle body from the outer holder.

In some embodiments, the manual safety injector further includes a skin sensor retained by the middle body and the outer holder, the skin sensor moveable between a first position where the skin sensor extends out distally past the foot of the outer holder and a second position where the skin sensor does not extend out distally past the foot of the outer holder.

In some embodiments, the skin sensor comprises a U-shaped slide member including a cross-bracket having a first end and a second end, a first sliding guide positioned at the first end of the cross-bracket and extending proximally from the cross-bracket, and a second sliding guide positioned at the second end of the cross-bracket and extending proximally from the cross-bracket, wherein the first and second sliding arms slide proximally within guide grooves on the middle body to move the skin sensor from the first position to the second position.

In some embodiments, the injector assembly further comprises a safety cap affixed to the distal-facing surface of the foot, the safety cap including a cover applied over the distal-facing surface of the foot, the cover including a needle opening and a pair of arm openings therein, the first and second sliding arms extending through the arm openings. The safety cap also includes a pull tab extending over distally from the cover and including a grip configured to be pulled by a user and a pair of concentric receptacles formed in a portion of the cover, the pair of receptacles including a first larger receptacle sized and arranged to accommodate a portion of the skin sensor therein when the skin sensor is in the first position and a second receptacle positioned within the first receptacle and sized and arranged to receive the needle cap therein.

In some embodiments, the distal-facing surface of the foot further comprises a depression formed therein configured to receive the cross-bracket when the skin sensor is in the second position.

In some embodiments, each of the inner container holder, the middle body, and the outer holder includes one or more windows therein that enable viewing of the container and a position of the stopper.

In some embodiments, after the additional actuation of the plunger assembly, the plunger assembly is locked in position by the injector assembly.

In some embodiments, the biasing member comprises a spring configured to transition from a compressed state to an extended state, the spring transitioning from the compressed state to the extended state to move the container assembly, the inner container holder, and the middle body distally within the outer holder, and thereby retract the sharp distal end of the needle back into the outer holder.

DESCRIPTION OF THE INVENTION

Figure 1:
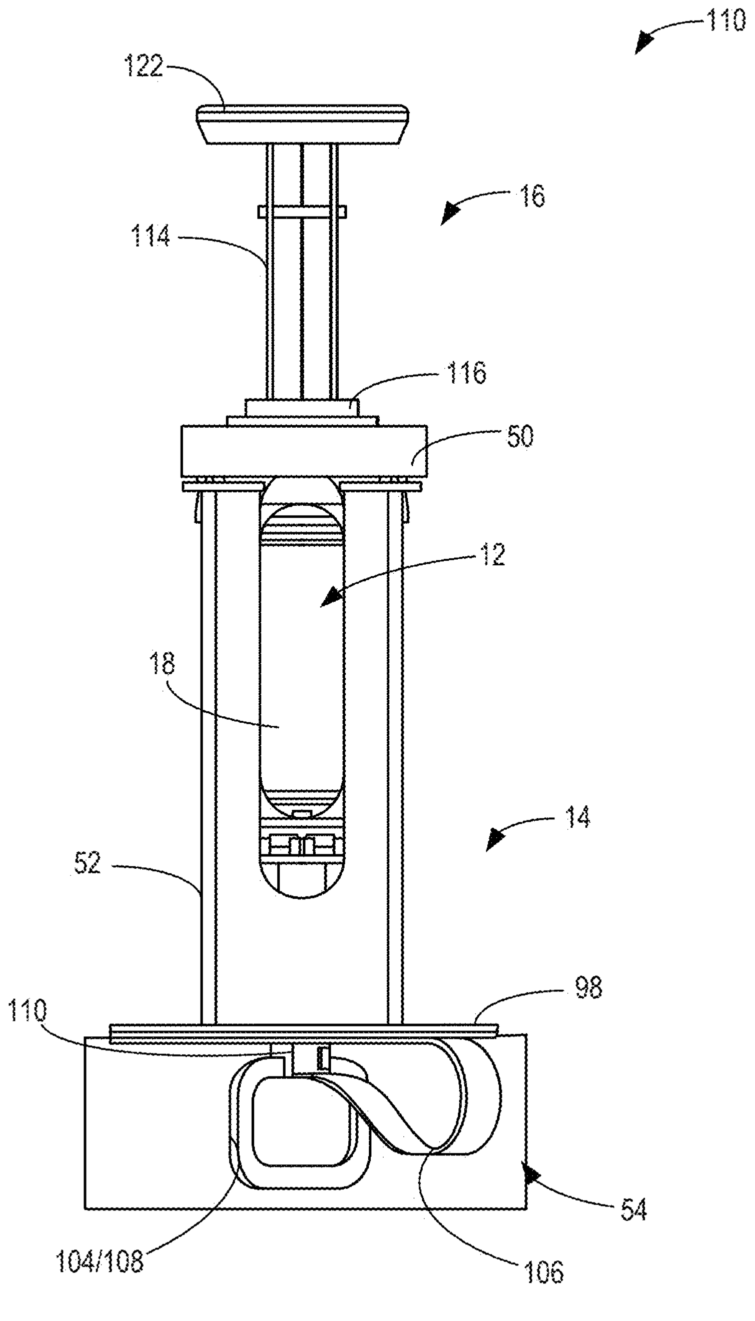
FIG. 1 is a perspective view of a 5-10 mL manual safety injector, according to a non-limiting embodiment described herein.
Figure 2:
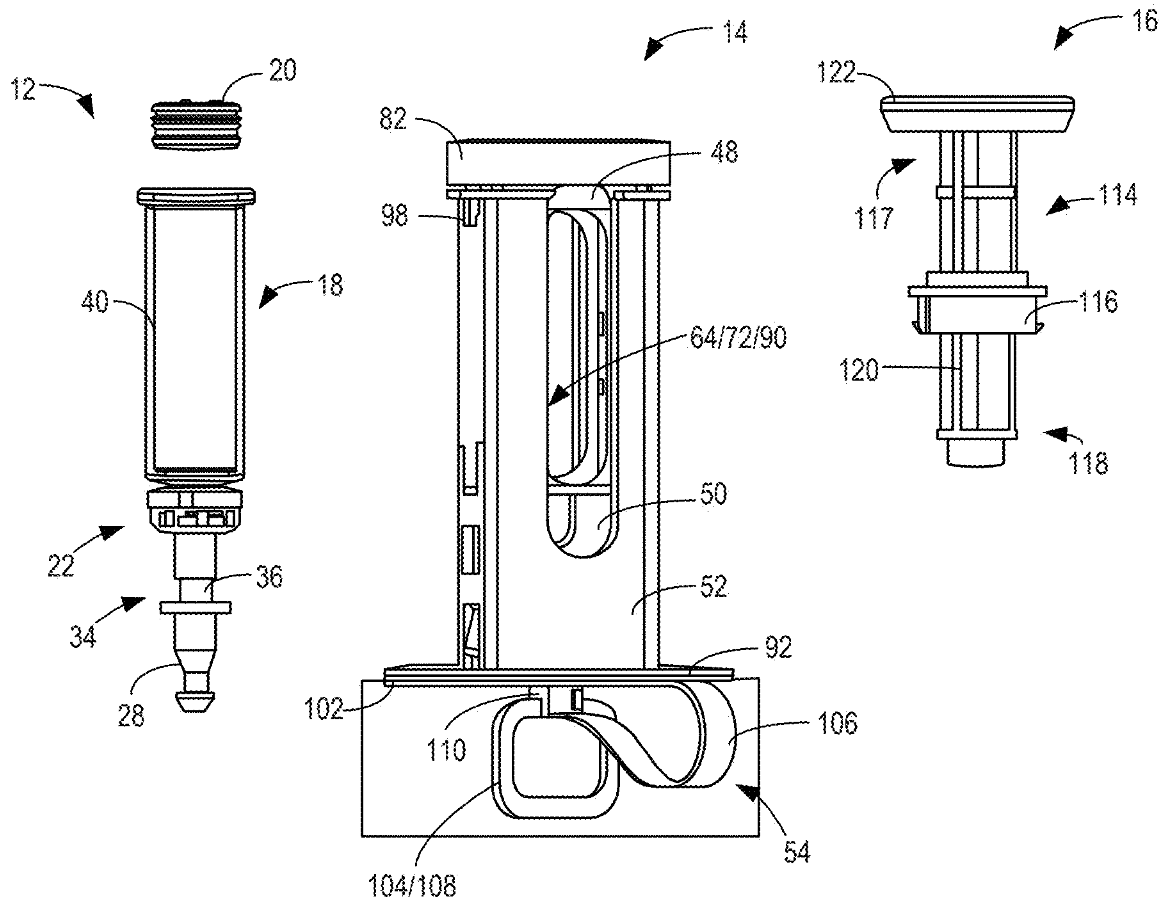
FIG. 2 is an exploded view of the safety injector of FIG. 1 showing a container assembly, injector assembly, and plunger assembly.
Figure 3:
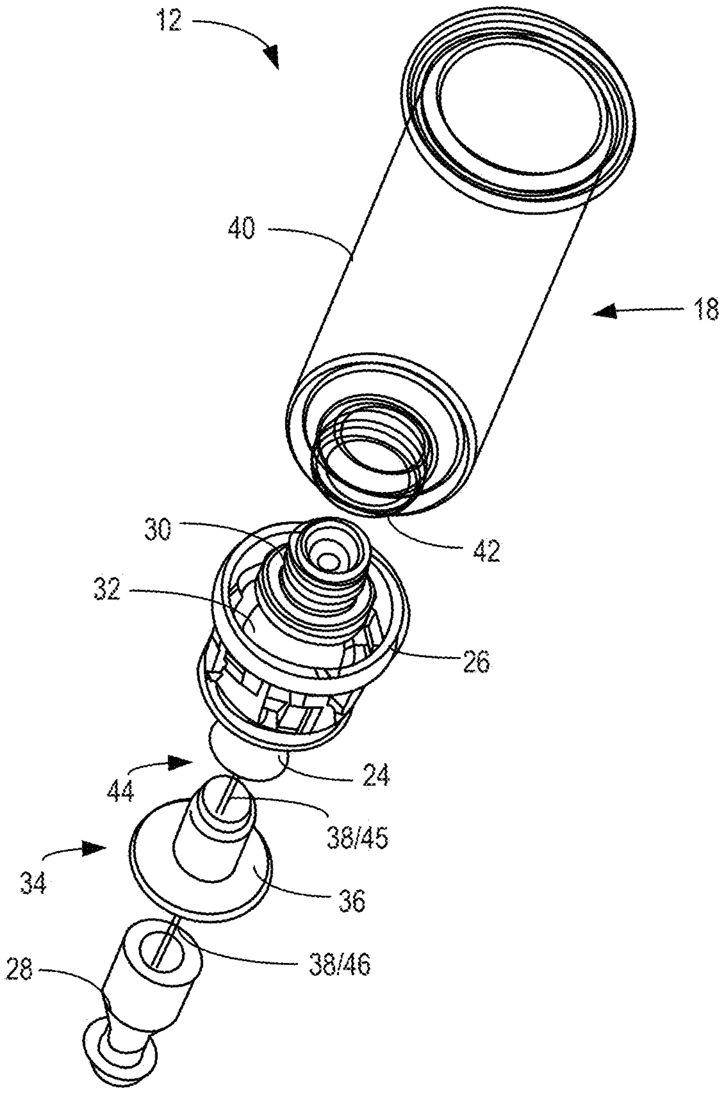
FIG. 3 is an exploded view of the container assembly of FIG. 2.
Figure 4:
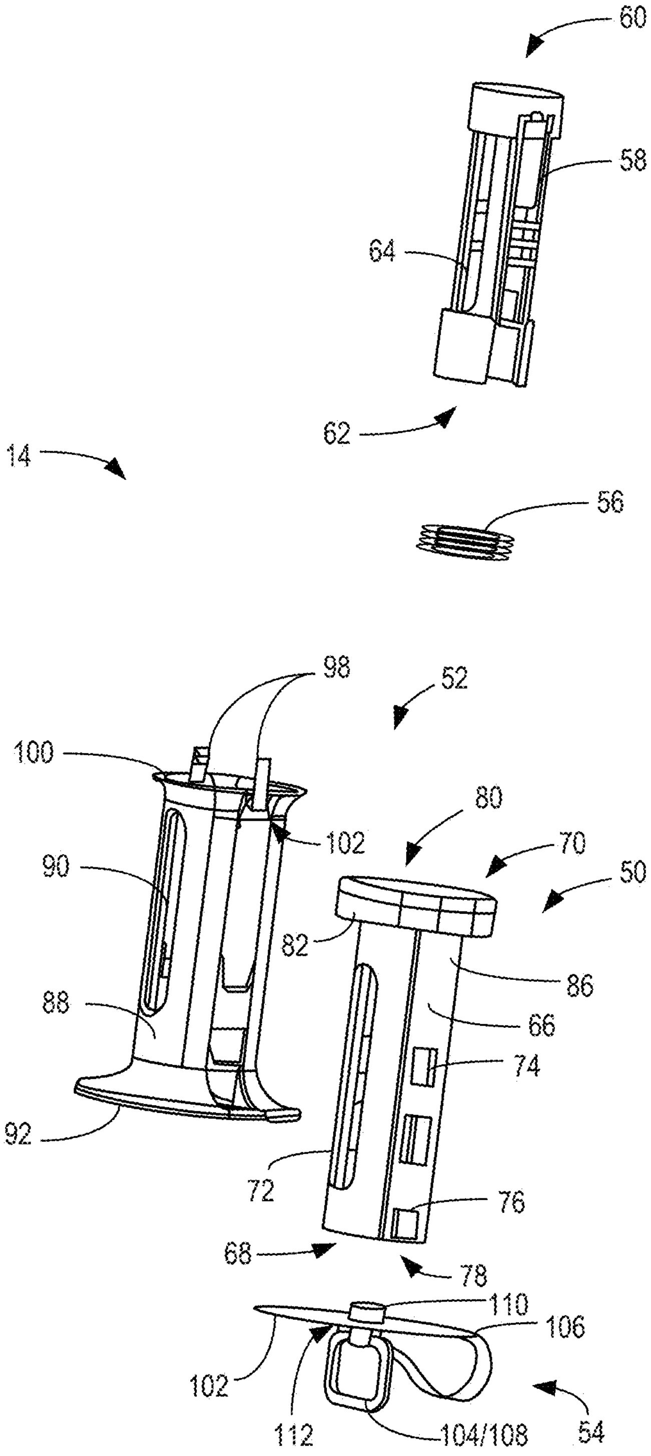
FIG. 4 is an exploded view of the injector assembly of FIG. 2.
Figure 5:
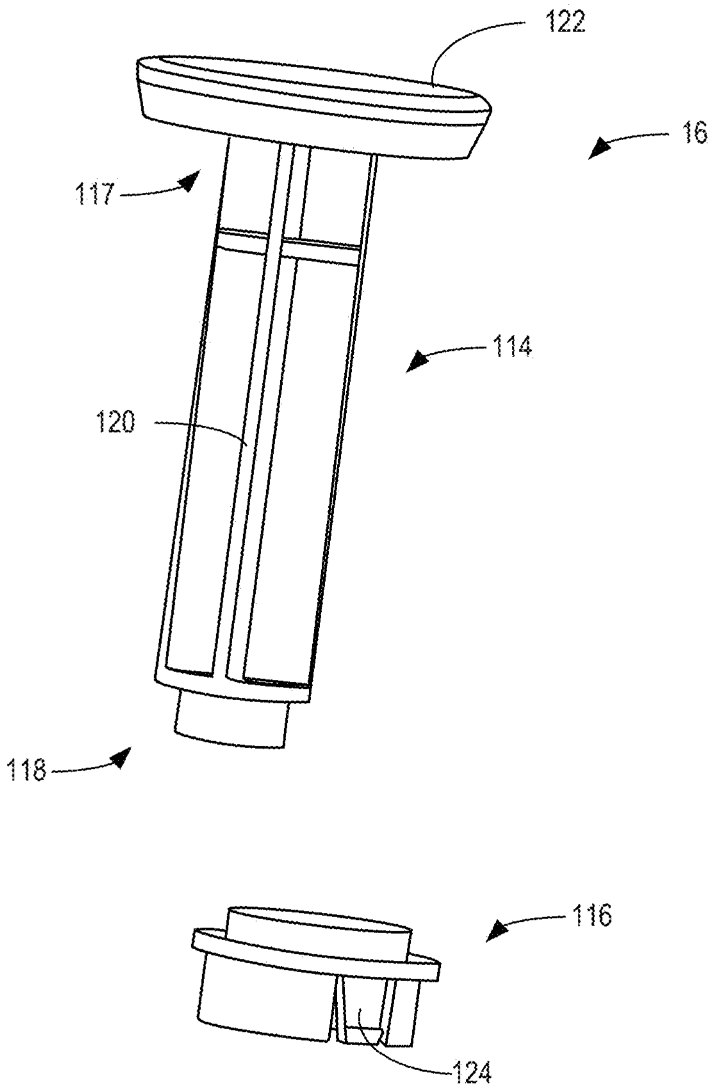
FIG. 5 is an exploded view of the plunger assembly of FIG. 2.

The following description is provided to enable those skilled in the art to make and use the described embodiments contemplated for carrying out the invention. Various modifications, equivalents, variations, and alternatives, however, will remain readily apparent to those skilled in the art. Any and all such modifications, equivalents, variations, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

As used in this specification, the words "proximal" and "distal" refer to the direction closer to and away from, respectively, a user who would place the device into contact with a patient. Thus, for example, the end of a device first touching the body of the patient would be the distal end, while the opposite end of the device being manipulated by the user would be the proximal end of the device. A "longitudinal direction" refers to the direction aligned with or extending between the distal end and the proximal end.

The terms "first", "second", and the like are not intended to refer to any particular order or chronology, but refer to different conditions, properties, or elements.

According to aspects of the disclosure, various embodiments of a manually operated/activated safety injector are provided for injecting a medicament into a patient. The safety injectors are configured to provide for the self-administering of a 5-10 mL dosage of medicament in a manner that is safe, user-friendly, and convenient for a patient. One or more of the safety injectors may include features thereon that enable the safety injector to be secured to the skin of the patient during injection, and that enable the patient to perform a controlled injection over a desired period of time.

In the various safety injector embodiments described here below, numerous components therein may be common to the different embodiments. Such components are identified in the description and the drawings using common numbers throughout the various embodiments.

Referring to FIGS. 1-6, shown is a non-limiting embodiment of a manually operated/activated safety injector 10 for injecting a medicament into a patient. The safety injector 10 is configured to provide for the self-administering of a 5-10 mL dosage of medicament in a manner that is safe, user-friendly, and convenient for a patient.

The safety injector may be characterized as generally including a container assembly 12, an injector assembly 14, and a plunger assembly 16, that may be pre-assembled by a manufacturer prior to receipt and use by a patient or other end user.

The container assembly 12 includes a container 18 with a stopper 20 positioned and retained therein, a cap assembly 22 comprising a tip cap needle holder 24 and a protective cap 26, a needle cap 28, a septum 30, a pierceable membrane 32, and a needle assembly 34 comprising a hub 36 and a double-ended needle cannula 38 (hereafter "needle 38"). According to embodiments, the container 18 may be provided as a standard cartridge or barrel. The container 18 may be provided as a pre-filled container that contains a volume of medicament or other fluid therein. As described above, the container 18 may contain a medicament or other fluid therein in the amount of 5-10 mL, such that the container 18 may be provided as a 5 mL cartridge/barrel, a 7 mL cartridge/barrel, or a 10 mL cartridge/barrel, as non-limiting examples.

The container 18 may comprise a cylindrical-shaped container body 40 defining an inner volume, with the container body 40 having an open proximal end and a distal end with a port 42 provided thereat. A coated septum 30 may be positioned at the distal end of the container body 40 and seated within the port 42, to seal the container 18. The stopper 20 is retained within the inner volume of the container 18, such as toward the proximal end of the container 18, with the stopper 20 positioned within the container 18 via a known stoppering technique (e.g., vent tube stoppering). With the septum 30 and the stopper 20 sealing the distal and proximal ends of the stopper 20, a medicament (or other fluid) that was pre-filled into the container body 40 may be retained in the container 18.

The cap assembly 22 is positioned at the distal end of the container body 40 and is positioned about/over the septum 30, with the septum 30 thus seated within the cap assembly 22. The cap assembly 22 is formed via coupling of the protective cap 26 and the tip cap needle holder 24, such as via an arrangement of clip provided on the protective cap 26, with the protective cap 26 positioned distally from the tip cap needle holder 24. The protective cap 26 may be positioned about and coupled to the port of container 18, to secure the cap assembly 22 to the container 18 and secure the septum 30 in place. The pierceable membrane 32 (e.g., a foil cover/seal) may be attached to a distal face of the protective cap 26 and cover a channel formed therethrough, so as to seal-off the septum 30 and maintain an aseptic condition thereof when the membrane 32 is intact. The tip cap needle holder 24 includes an annular seat 44 at the distal end thereof that is configured to receive a portion (i.e., a distal end) of the needle assembly 34.

As indicated above, the needle assembly 34 comprises a hub 36 and a needle 38. The needle 38 is retained within a hole formed through hub 36 and extends out both proximally and distally from the hub 36. A proximal end of the hub 36 is positioned within the annular seat 44 of the tip cap needle holder 24 and is seated therein. The hub 36 may be seated within annular seat 44 so as to movable therein if a sufficient force is applied against the hub 36. That is, the hub 36 may be moved proximally back and further into the annular seat 44 when a force is applied thereto. The needle 38 includes a proximal sharp end 45 that is positioned within an internal volume of the annular seat 44 and an opposed distal sharp end 46 that is initially received within (and covered by) the needle cap 28. The distal end 46 is used for aspiration or injection of the medicament contained within container 18 into a patient.

The injector assembly 14 includes an inner container holder 48, a middle body 50, an outer holder 52, a safety cap 54, and a biasing member or spring 56.

The inner container holder 48 of the injector assembly 14 may comprise a generally elongated member that is configured to receive and retain the container assembly 12 therein. The inner container holder 48 may comprise a tube-shaped body 58 having an open proximal end 60 and an open distal end 62. The tube-shaped body 58 includes one or more windows 64 therein through which the container 18 may be viewed. The container assembly 12 may be introduced into the inner container holder 48 via the open proximal end 60, and may be advanced distally through the inner container holder 48 until a distal end of the container body 40 abuts a retainer (e.g., retaining clips or arms, extending radially inward from the tube-shaped body 58) formed at the distal end of the inner container holder 48. The cap assembly 22 and needle assembly 34 may then protrude distally out past the inner container holder 48.

The middle body 50 of the injector assembly 14 is positioned about the inner container holder 48 and receives inner container holder 48. The inner container holder 48 is received with the middle body 50 so as translatable therein in the longitudinal direction. The middle body 50 may generally comprise a sidewall structure 66, a distal end member 68, and a proximal end member 70.

The sidewall structure 66 includes one or more windows 72 therein through which the container 18 may be viewed, with the window(s) 72 of the middle body 50 aligned with the window(s) 64 of the inner container holder 48. Additionally, a plurality of flexible/bendable release tabs may be formed on the sidewall structure 66. A first pair of release tabs 74 may be angled radially inward (relative to a remainder of the sidewall structure 66) and function to selectively engage the inner container holder 48, to selectively allow or inhibit movement of the inner container holder 48 relative to the middle body 50. A second pair of release tabs 76 may be angled radially outward (relative to a remainder of the sidewall structure 66) and function to selectively engage the outer holder 52, to selectively allow or inhibit movement of the middle body 50 relative to the outer holder 52.

The distal end member 68 of middle body 50 partially encloses the distal end of the middle body 50, but includes an opening 78 formed therein. The opening 78 in distal end member 68 accommodates positioning of the needle cap 28 therein, and allows for the needle assembly 34 to extend/protrude therethrough when the inner container holder 48 is moved distally through the middle body 50, as explained in further detail below.

The proximal end member 70 of middle body 50 partially encloses the proximal end of the middle body 50, but includes an opening 80 formed therein. The opening 80 in proximal end member 70 accommodates positioning of the plunger assembly 16 therein. The proximal end member 70 comprise a flanged portion 82 that extends radially outward from the sidewall structure 66. The flanged portion 82 may include a pair of openings 84 therein that receive elements of the outer holder 52 therein, as explained in further detail below.

In some embodiments, the sidewall structure 66 may include a visual indicator 86 thereon that may indicate to a user when delivery of the medicament within container 18 is complete. The visual indicator 86 may be in the form of a brightly colored line or symbol, for example, that is provided on the sidewall structure 66 near the proximal end member 70—with the visual indicator 86 becoming visible to the user upon a full depressing of the plunger assembly 16 and a movement of the middle body 50 relative to the outer holder 52, as explained in further detail below.

The outer holder 52 of the injector assembly 14 has a tube-shaped main holder body 88 sized to receive the middle body 50 therein. Similar to the middle body 50 and the inner container holder 48, the holder body 88 of outer holder 52 includes one or more windows 90 therein through which the container 18 may be viewed, with the window(s) 90 of the outer holder 52 aligned with the window(s) 72, 64 of the middle body 50 and the inner container holder 48.

A foot 92 is provided on the outer holder 52 at the distal end of the holder body 88. The foot 92 may comprise a circular member that extends radially outward past the holder body 88. The foot 92 may substantially close the distal end of the holder body 88, but includes a needle opening 94 therein that accommodates positioning of the needle cap 28 therein, and allows for the needle 38 to extend/protrude therethrough when the inner container holder 48 is moved distally through the middle body 50, as explained in further detail below. A distal-facing surface of the foot 92 may comprise a generally flat surface and may be configured as a textured surface having a plurality of ribs—with the distal-facing surface configured to accommodate placement of the safety injector 10 against the skin of a patient when in use. According to embodiments, the distal-facing surface may comprise an adhesive patch 96 (e.g., a biocompatible adhesive foam pad) that covers a portion or all of the distal-facing surface. The adhesive patch 96 allows for the safety injector 10 to be secured to the skin of a patient, providing improved stability of the safety injector 10 during use.

The proximal end of the holder body 88 includes a pair of hook members 98 that extend out in a proximal direction. The hook members 98 are aligned with the pair of openings 84 formed in the flanged portion 82 of the proximal end member 70 of middle body 50, with the hook members 98 configured to extend through the openings 84 and engage the proximal end member 70 on a proximal-facing surface thereof-thereby securing the outer holder 52 to the middle body 50.

In some embodiments, a fluted upper lip 100 may be provided at the proximal end of the holder body 88. The upper lip 100 may taper radially outward from the holder body 88, with the upper lip 100 having an outer diameter that is substantially the same as an outer diameter of the flanged portion 82 of the proximal end member 70 on middle body 50. Gaps 102 are formed in the upper lip to accommodate the inclusion of hook members 98. The upper lip 100 may function as a finger fillet that provides for syringe-style gripping of the safety injector 10 by a user.

The safety cap 54 of the injector assembly 14 is affixed to the foot 92 and includes a cover 102, a pull tab 104, and a loop 106 connecting the pull tab 104 and the cover 102. The cover 102 of safety cap 54 has a surface area identical to the foot 92 and is configured to lay flat on and completely cover 102 the foot 92 when positioned thereover. The pull tab 104 may be configured to extend out distally from the cover 102, with the pull tub including a grip 108 with which the finger of a patient may be engaged, to provide for pulling of the safety cap 54 off from the outer holder 52. The pull tab 104 further includes a receptacle 110 that extends out proximally from the grip 108, with the receptacle 110 extending through an opening 112 formed in cover 102 and being configured to receive the needle cap 28 therein. When the pull tab 104 is pulled distally away from cover 102 (and out of opening 112 therein), the needle cap 28 may be retained within receptacle 110, allowing for the needle cap 28 to be removed from over the needle 38. The loop 106 connects the grip 108 to an edge of the cover 102, such that when a user engages the grip 108, a continued pulling force applied to the grip 108 is transferred to the cover 102 (via the loop 106), such that the cover 102 may be pulled off from the foot 92. Removal of the safety cap 54 from the outer holder 52 in this manner thus uncovers the adhesive patch 96 on foot 92 and also uncovers the needle 38, to allow for a subsequent injection to be performed.

As best shown in FIGS. 6A-6E, the spring 56 of injector assembly 14 is retained between the middle body 50 and the outer holder 52. Specifically, the spring 56 is retained between a distal-facing surface of middle body 50 (i.e., on a distal-facing surface of distal end member 68) and a proximal-facing surface of foot 92. With the safety injector 10 in an initial configuration (prior to any actuation thereof), the spring 56 is retained in a compressed state. As explained in further detail below, the spring 56 may actuate from the compressed state to an extended (or partially extended) state upon completion of an injection, so as to force middle body 50 back proximally within outer holder 52 and thereby provide shielding to the needle 38 after completion of the injection.

The plunger assembly 16 includes a plunger rod 114 and a plunger retainer 116 that is positioned about the plunger rod. The plunger rod 114 may include a main body extending between a plunger rod proximal end 117 and a plunger rod distal end 118. In some embodiments, the main body may include a plurality of elongate vanes or walls 120 extending axially along a length thereof between the plunger rod proximal end 117 and the plunger rod distal end 118. A thumb press 122 is positioned at the plunger rod proximal end 117 that may be engaged by a thumb (or other finger) of the user to apply a distally directed force to the plunger rod 114, to move the plunger rod 114 with respect to the container 18—i.e., advance the plunger rod (and stopper 20) distally into the container 18. In some embodiments, the thumb press 122 may have a concave profile and/or include ridges formed thereon, to improve engagement between a thumb and the thumb press 122. The plunger rod distal end 118 is configured to mate with the stopper 20 positioned in container 18 and, in some embodiments, may include a flanged extension that engages a cavity formed in the stopper 20.

The plunger retainer 116 may be positioned on the main body of plunger rod 114, with an opening formed through the plunger retainer 116 through which the plunger rod 114 extends. The plunger retainer 116 is configured to engage the inner container holder 48, to secure the plunger retainer 116 to the injector assembly 14. In some embodiments, the plunger retainer 116 may include a pair of hooks 124 formed thereon that engage hook openings formed in the tube-shaped body 58 of inner container holder 48, adjacent the proximal end thereof. The plunger retainer 116 may thus function to properly align the plunger rod 114 with the container assembly 12, to enable engagement of the plunger rod 114 with the stopper 20 and provide for linear movement of the plunger rod 114 relative to the container 18.

Referring now to FIGS. 6A-6E, operation of the safety injector 10 is described in more detail. As indicated above, the safety injector 10 is pre-assembled by a manufacture, so as to be provided to a user in a ready to use condition.

Figure 6A:
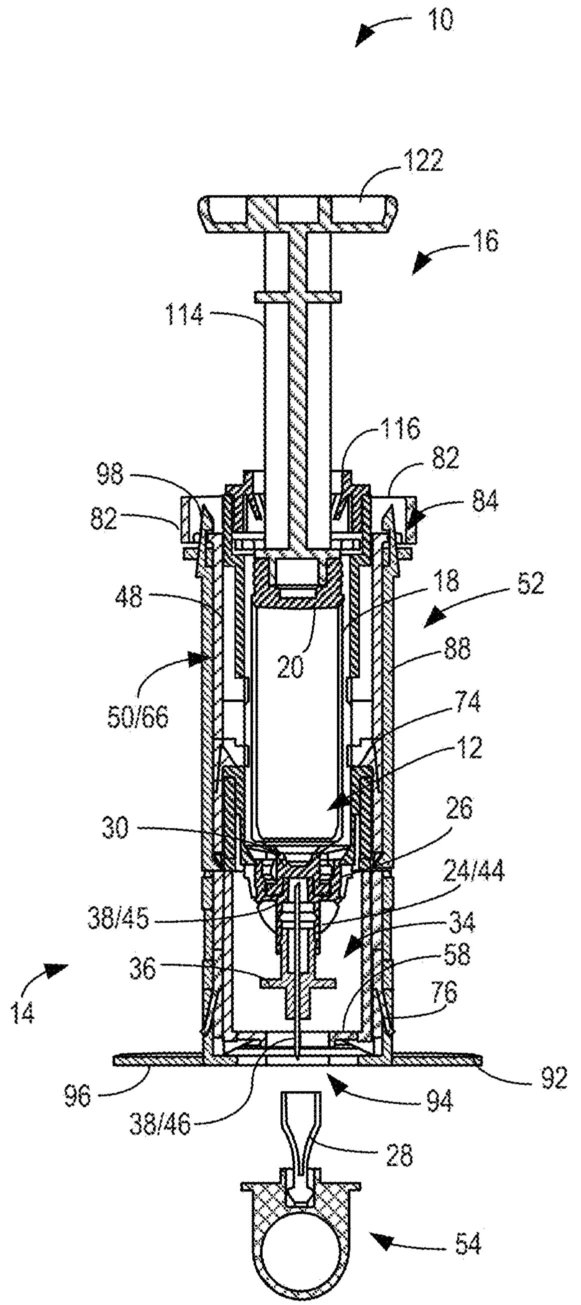
FIGS. 6A-6E are side cross-sectional views of the safety injector of FIG. 1, with the safety injector in different operational states.

From an initial configuration of the safety injector 10, as shown in FIG. 6A, a user will first remove the safety cap 54 and needle cap 28 from the injector. Removal of the safety cap 54 uncovers the adhesive patch 96 on the distally facing surface of the foot 92, to allow for adhering/securing of the safety injector 10 to the skin of the patient.

Figure 6B:
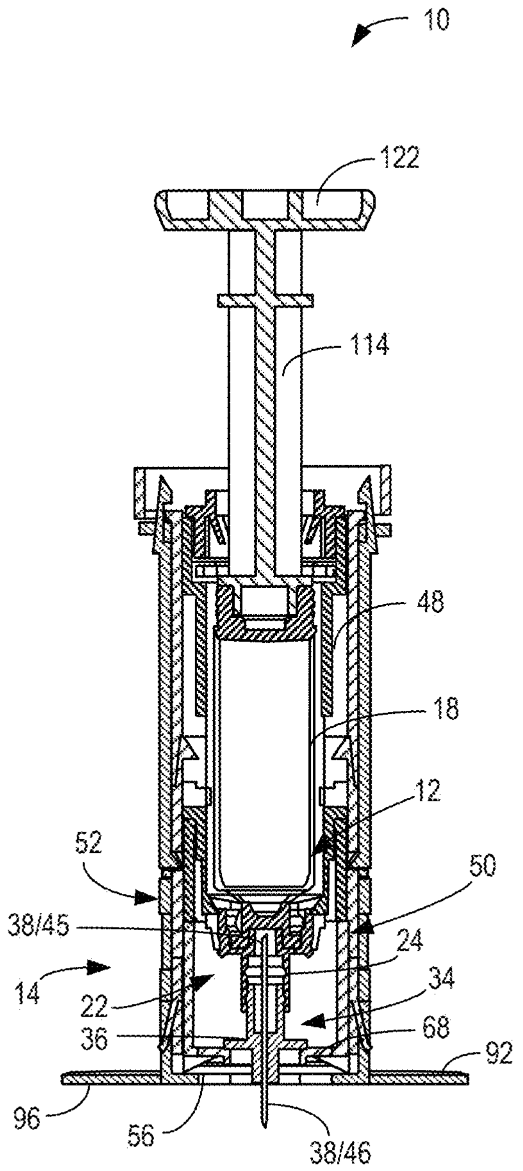

With the safety cap 54 and needle cap 28 removed from the safety injector 10, the safety injector 10 may be adhered to the skin of the patient, and the needle 38 may then be inserted into the patient, as shown in FIG. 6B. Insertion of the needle 38 is achieved by application of an initial, distally-directed pressure to the plunger rod 114, with this pressure causing the inner container holder 48 (and the container assembly 12 retained therein) to move distally further into the middle body 50. Specifically, application of an initial, distally-directed pressure to the plunger rod 114 causes the first pair of release tabs 74 on middle body 50 to become disengaged from the inner container holder 48, thereby providing for distal movement of the inner container holder 48 and the container assembly 12 within the middle body 50. With the container assembly 12 (and inner container holder 48) moved distally within the middle body 50, the needle 38 is caused to protrude out distally from the outer holder 52, such that the needle 38 is injected into the patient with a controlled depth of penetration (i.e., the amount the needle 38 extends out past outer holder 52/foot 92).

Figure 6C:
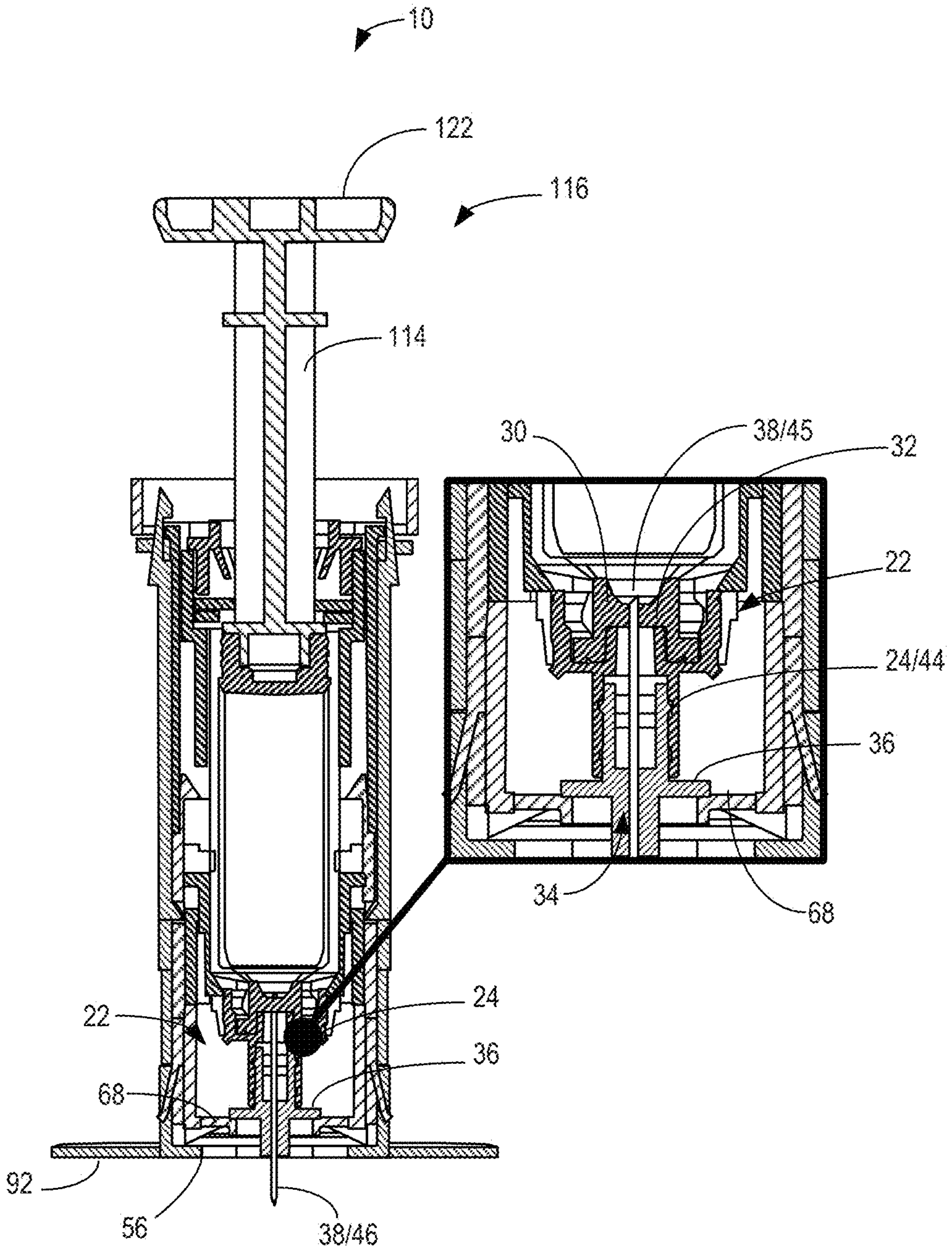

As part of the same initial, distally-directed pressure applied to the plunger rod 114, the needle assembly 34 may be caused to move proximally relative to cap assembly 22, in order to place the needle 38 in fluid communication with the container 18, as shown in FIG. 6C. That is, as the needle 38 is inserted into the patient during application of the initial, distally-directed pressure to the plunger rod 114, the hub 36 of needle assembly 34 comes into contact with the distal end member 68 of middle body 50, such that the continued application of a distally-directed pressure to the plunger rod 114 causes the hub 36 to be pushed back proximally further into the annular seat 44 of the tip cap needle holder 24. As the hub 36 is pushed proximally back into the tip cap needle holder 24, the proximal end 45 of the needle 38 is caused to be driven through the pierceable membrane 32 and through the septum 30, so as to place the needle 38 in fluid communication with the inner volume of container 18.

Figure 6D:
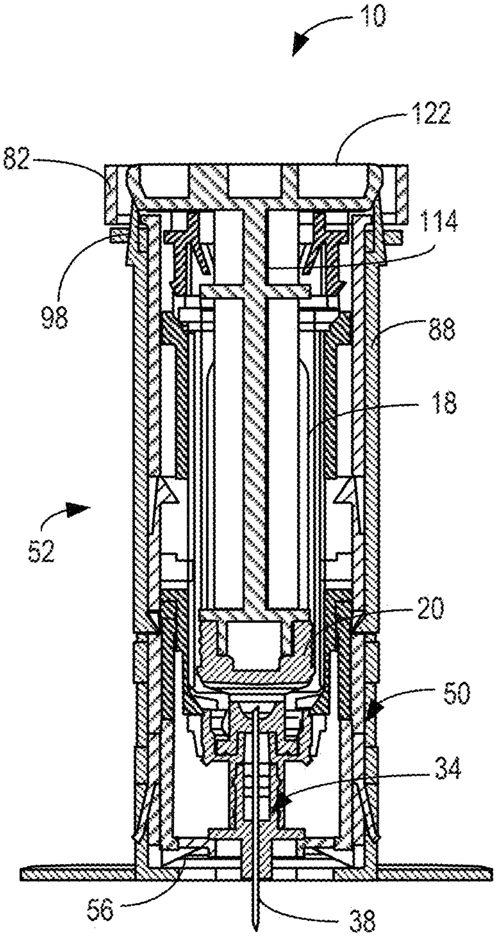

As shown in FIG. 6D, upon placing of the needle 38 in fluid communication with the container 18, a continued distally-directed pressure may be applied to the plunger rod 114 by a user, to force the medicament out from the container 18 and through the needle 38, for administering to the patient. That is, the user may continue to advance the plunger rod 114 and stopper 20 distally into the container 18, thereby forcing the medicament out from the container 18 and through the needle 38.

Figure 6E:
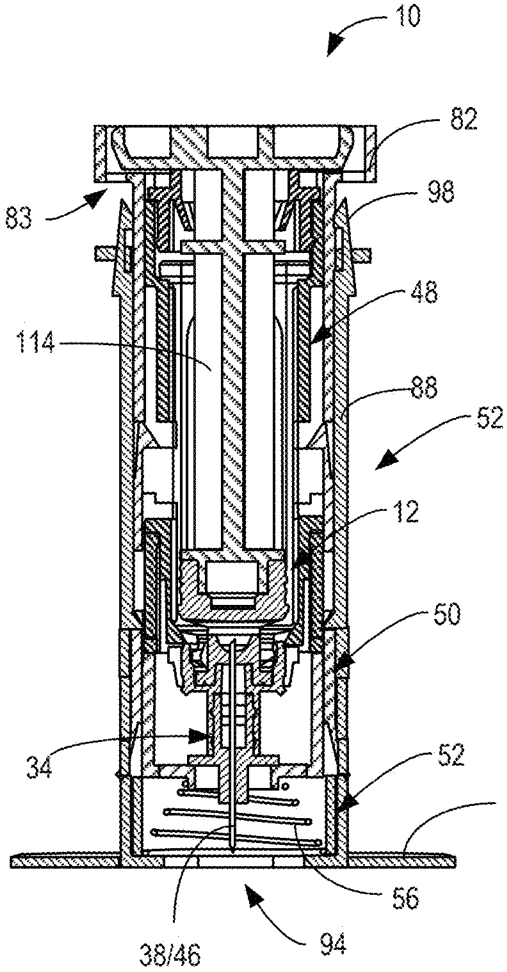

As the plunger rod 114 is approaching being fully depressed into the container 18, a distally-facing surface of the thumb press 122 of the plunger rod 114 is brought into contact with the pair of hook members 98 that extend out in a proximal direction from the holder body 88 of outer holder 52. The thumb press 122 applies a distally directed force to the hook members 98, thereby causing the hook members 98 to become disengaged from the flanged portion 82 of the proximal end member 70 of middle body 50, such that the hook members 98 slide out through the pair of openings 84 formed in the flanged portion 82. With the hook members 98 forced out through the pair of openings 84, the middle body 50 is disengaged from the outer holder 52, thereby allowing for the spring 56 to be released and transition from its compressed state to its extended state. As the spring 56 transitions from its compressed state to its extended state, the middle body 50 is pushed back proximally within the outer holder 52, as shown in FIG. 6E, with the second pair of release tabs 76 also disengaging from outer holder 52, to allow the proximal movement of the middle body 50 relative to the outer holder 52. With the middle body 50 moved back proximally within the outer holder 52, the container assembly 12—and the needle assembly 34 thereof—is also caused to move back proximally, such that the needle 38 is retracted from the patient and back into the outer holder 52 (through needle opening 94 in foot 92). With the container assembly 12 and needle assembly 34 retracted back proximally, the distal end 46 of the double-ended needle 38 is positioned within the outer holder 52, so as to cover the distal end 46 of the needle 38. Additionally, once the plunger rod 114 is advanced to the fully depressed position, the plunger rod 114 locks, so as to prevent re-use of the safety injector 10.

In some embodiments, the proximal movement of the middle body 50 within the outer holder 52 causes the visual indicator 86 (e.g., colored line or symbol) provided near the proximal end of the sidewall structure 66 of the middle body 50 to become visible (i.e., extend out past the outer holder 52). The visual indicator 86 may thus confirm to the user that the injection of the medicament is complete.

Figure 7:
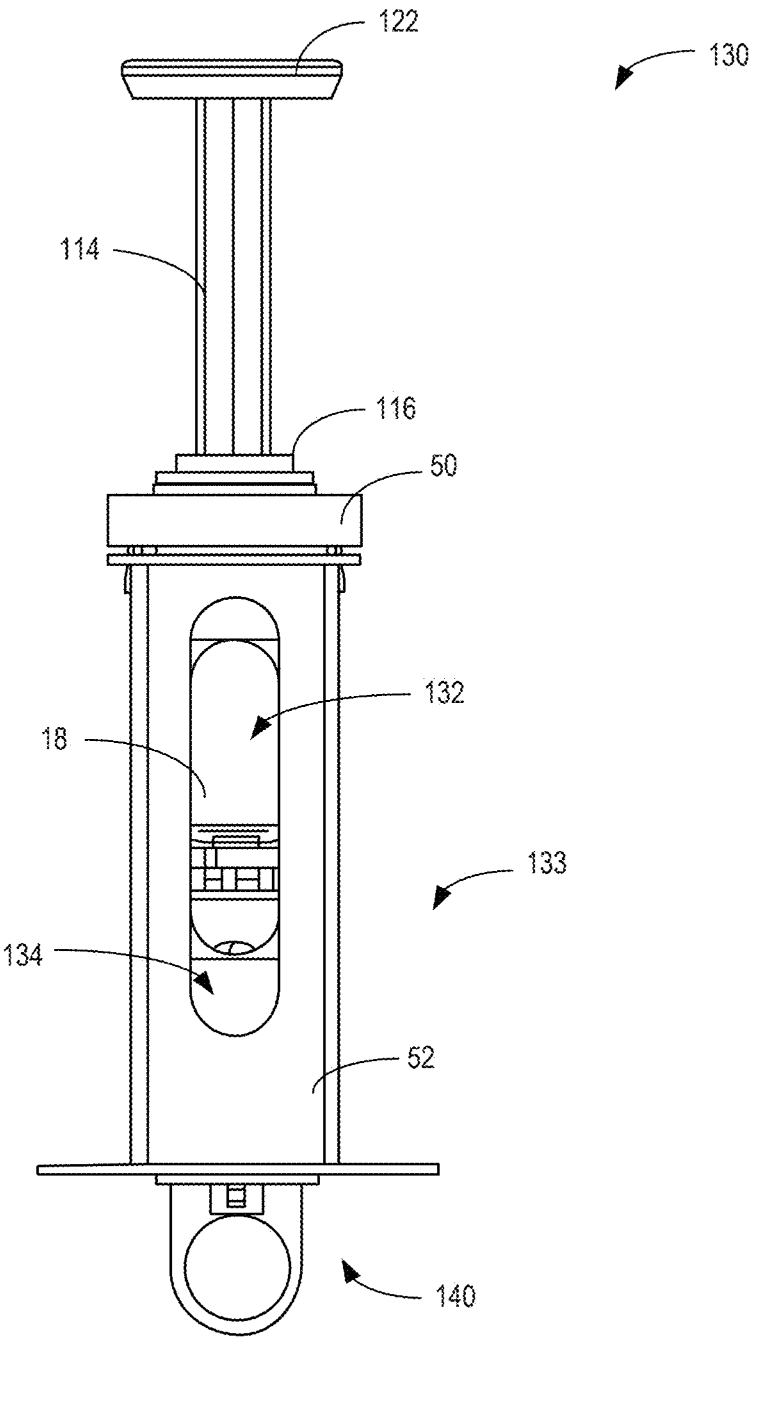
FIG. 7 is a perspective view of a 5-10 mL manual safety injector, according to another non-limiting embodiment described herein.
Figure 8:
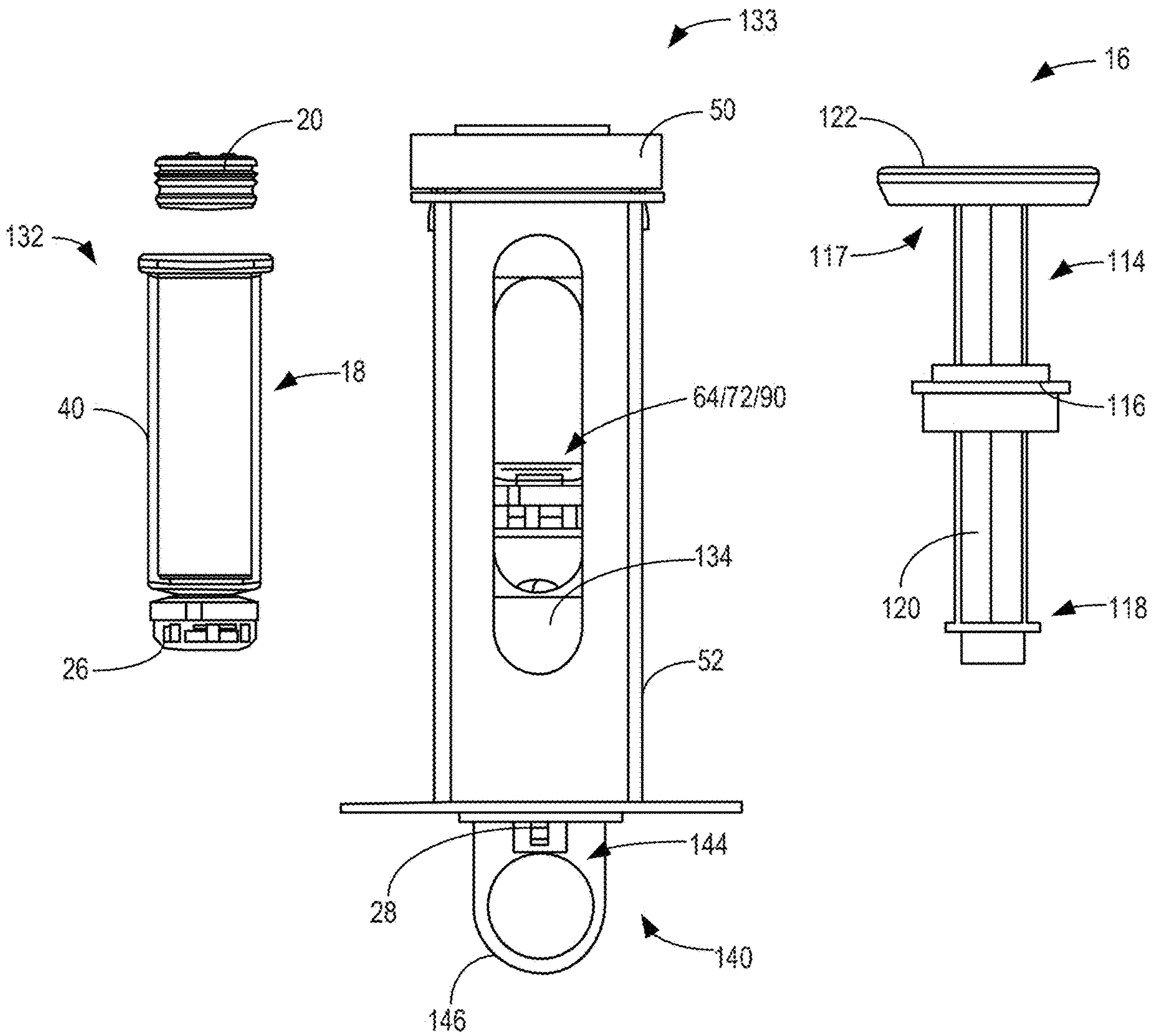
FIG. 8 is an exploded view of the safety injector of FIG. 7 showing a container assembly, injector assembly, and plunger assembly.

Referring now to FIGS. 7-9, shown is another non-limiting embodiment of a manually operated/activated safety injector 130 for injecting a 5-10 mL dosage of medicament into a patient. The safety injector 130 may be characterized as generally including a container assembly 132, an injector assembly 133, and a plunger assembly 16, that may be pre-assembled by a manufacturer prior to receipt and use by a patient or other end user.

The container assembly 132 includes a container 18 (i.e., a cartridge or barrel) with a stopper 20 positioned and retained therein, a protective cap 26, a septum 30, and a pierceable membrane 32. The container 18 may be provided as a pre-filled cartridge or barrel that contains a volume of medicament or other fluid therein. As described above, the container 18 may contain a medicament or other fluid therein in the amount of 5-10 mL, such that the cartridge/barrel may be provided as a 5 mL cartridge/barrel, a 7 mL cartridge/barrel, or a 10 mL cartridge/barrel, as non-limiting examples.

The container 18 may comprise a cylindrical-shaped container body 40 defining an inner volume, with the container body 40 having an open proximal end and distal end with a port 42 provided thereat. A coated septum 30 may be positioned at the distal end of the container body 40 and seated within the port 42, so as to seal the container 18 at the distal end. The stopper 20 is retained within the inner volume of the container 18, such as toward the proximal end of the container 18, with the stopper 20 positioned within the container 18 via a known stoppering technique (e.g., vent tube stoppering). With the septum 30 and the stopper 20 sealing the distal and proximal ends of the container 18, a medicament (or other fluid) that was pre-filled into the container body 40 may be retained in the container 18.

The protective cap 26 is positioned at the distal end of the container body 40 and is positioned about/over the septum 30. The protective cap 26 may be positioned about and coupled to the port 42 of container 18, to secure the septum 30 in place. The pierceable membrane 32 (e.g., a foil cover/seal) may be attached to a distal face of the protective cap 26 and cover a channel formed therethrough, so as to seal-off the septum 30 and maintain an aseptic condition thereof when the membrane 32 is intact.

The injector assembly 133 includes an inner container holder 134, a middle body 50, an outer holder 52, a needle shield 140, a fluid transfer assembly 142 and a biasing member or spring 56. According to embodiments, the middle body 50, outer holder 52, and spring 56 of injector assembly 133 are constructed and arranged identically to the middle body 50, outer holder 52, and spring 56 of injector assembly 133 of the safety injector of FIGS. 1-6, and thus reference is made to the previous description of those components and not repeated here, with like numbers used to identify those components in FIGS. 7-9.

The needle shield 140 of the injector assembly 133 may comprise a pull tab 144 and a needle cap 28. The pull tab 144 includes a grip 146 with which the finger of a patient may be engaged, to provide for pulling of the needle shield 140 off from the outer holder 52. The pull tab 144 further includes a proximally facing surface that may engage the foot 92 of outer holder 52, with the proximally facing surface also including a receptacle 148 therein. The receptacle 148 is configured to receive and retain the needle cap 28 therein, with the needle cap 28 extending through opening 94 in the foot 92 to mate with the fluid transfer assembly 142 (and be positioned over a needle thereof). When the pull tab 144 is pulled distally away from the outer holder 52, the needle cap 28 may be retained within receptacle 136, allowing for the needle cap 28 to be removed from over the needle of the fluid transfer assembly 142.

The fluid transfer assembly 142 generally includes a valve assembly 150 and a needle assembly 152, similar to what is described in International Publication No. WO 2015/081337, which is hereby incorporated by reference in its entirety. In brief, the valve assembly 150 includes a two-part flexible sleeve 154, while the needle assembly 152 includes a needle shield holder 156 and a needle cannula 38 (hereafter "needle 38") fixedly retained by the needle shield holder 156. In the embodiment of FIGS. 7-9, the needle 38 is provided as a double-ended needle cannula—with the needle 38 including a proximal sharp end 45 that is positioned within an internal volume of the valve assembly 150 and an opposed distal sharp end 46 that is initially received within (and covered by) the needle shield holder 156. Preferably, everything inside the flexible sleeve 154 is sterile.

The inner container holder 134 of the injector assembly 133 may comprise a generally elongated member that is configured to receive and retain the container assembly 132 and the fluid transfer assembly 142 therein. The inner container holder 134 may comprise a tube-shaped body 158 having an open proximal end 160 and an open distal end 162. The tube-shaped body 158 includes one or more windows 64 therein through which the container 18 may be viewed. The container assembly 132 may be introduced into the inner container holder 134 via the open proximal end 160, and may be advanced distally through the inner container holder 134 until a proximal lip or flange of the container body 40 abuts a retaining member formed at the proximal end of the tube-shaped body, such as a plurality of radially inward-directed clips formed on the tube-shaped body 158. The fluid transfer assembly 142 may be coupled to a distal end of the tube-shaped body 158, such as via securing of an outer circumferential edge of the needle shield holder 156 to the tube-shaped body 158. With the fluid transfer assembly 142 coupled to the distal end of the tube-shaped body 158, the valve assembly 150 may be positioned internally within the tube-shaped body 158, while a distal portion of the needle shield holder 156 and the distal end 46 of the needle 38 protrude distally out past the inner container holder 134.

With the container assembly 132 and the fluid transfer assembly 142 retained in the inner container holder 134 in an initial position, the container assembly 132 and the fluid transfer assembly 142 are arranged so as to be spaced apart in the longitudinal direction. That is, a gap is provided between the protective cap 26 and the valve assembly 150 with the container assembly 132 and the fluid transfer assembly 142 in an initial position within inner container holder 134. During use of the safety injection, the container assembly 132 may be caused to move distally within the inner container holder 134, thereby bringing the container assembly 132 into contact with the fluid transfer assembly 142, as explained in further detail below.

Regarding the plunger assembly 16 of safety injector, the plunger assembly 16 includes a plunger rod 114 and a plunger retainer 116 that are structured identically to those previously described in the safety injector of FIGS. 1-6. Accordingly, the plunger assembly 16 is not described in detail again here.

Referring now to FIGS. 9A-9E, operation of the safety injector 130 is described in more detail. As indicated above, the safety injector 130 is pre-assembled by a manufacture, so as to be provided to a user in a ready to use condition.

Figure 9A:
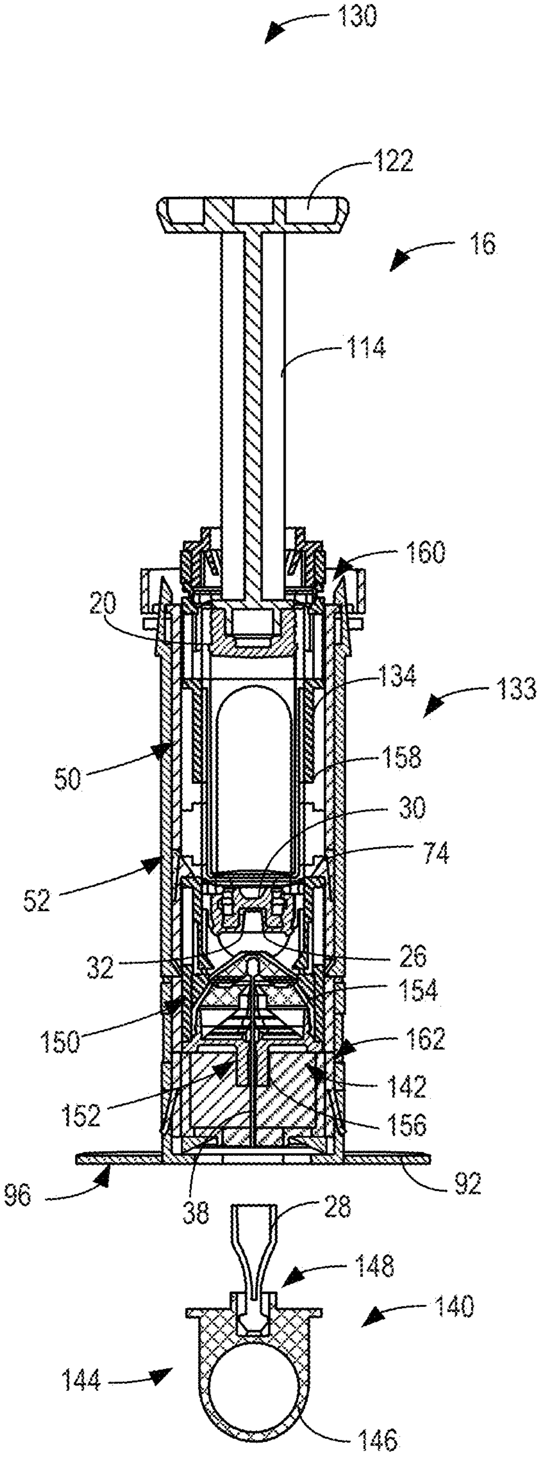
FIGS. 9A-9E are side cross-sectional views of the safety injector of FIG. 7, with the safety injector in different operational states.

From an initial configuration of the safety injector 130, as shown in FIG. 9A, a user will first remove the needle shield 140 (including needle cap 28) from the injector. In some embodiment, removal of the needle shield 140 may uncover an adhesive patch 96 on the distally facing surface of the foot, to allow for adhering/securing of the safety injector to the skin of the patient.

Figure 9B:
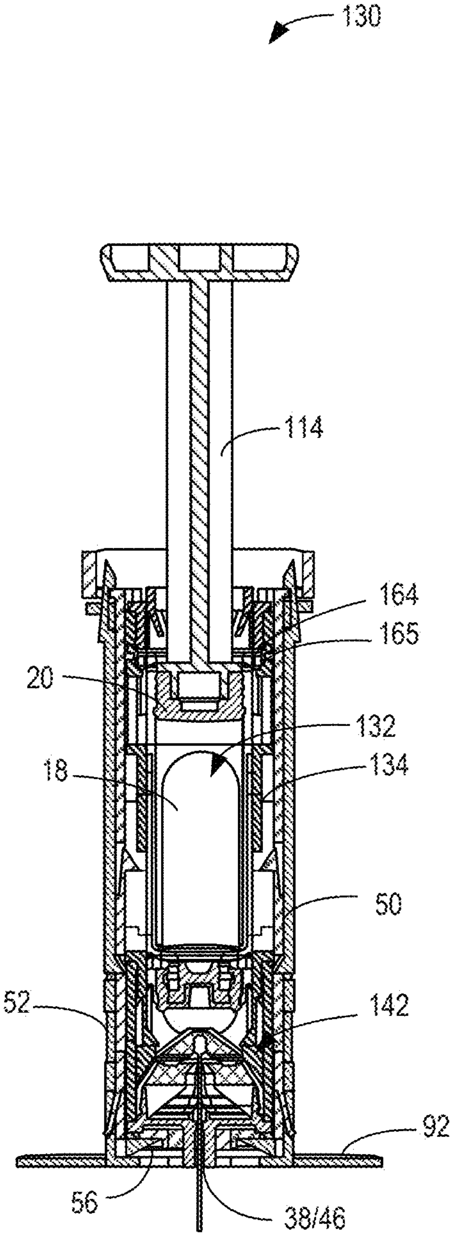

With the needle shield 140 removed from the safety injector, the safety injector 130 may be adhered to the skin of the patient, and the needle 38 may then be inserted into the patient, as shown in FIG. 9B. Insertion of the needle 38 is achieved by application of an initial, distally-directed pressure to the plunger rod 114, with this pressure causing the inner container holder 134 (and the container assembly 132 and fluid transfer assembly 142 retained therein) to move distally further into the middle body 50. Specifically, application of an initial, distally-directed pressure to the plunger rod 114 causes the first pair of release tabs 74 (FIG. 9A) on middle body 50 to become disengaged from the inner container holder 134, thereby providing for distal movement of the inner container holder 134 and the container assembly 132 within the middle body 50. With the container assembly 132 (and inner container holder 134) moved distally within the middle body 50, the needle 38 is caused to protrude out distally from the outer holder 52, such that the needle 38 is injected into the patient.

Figure 9C:
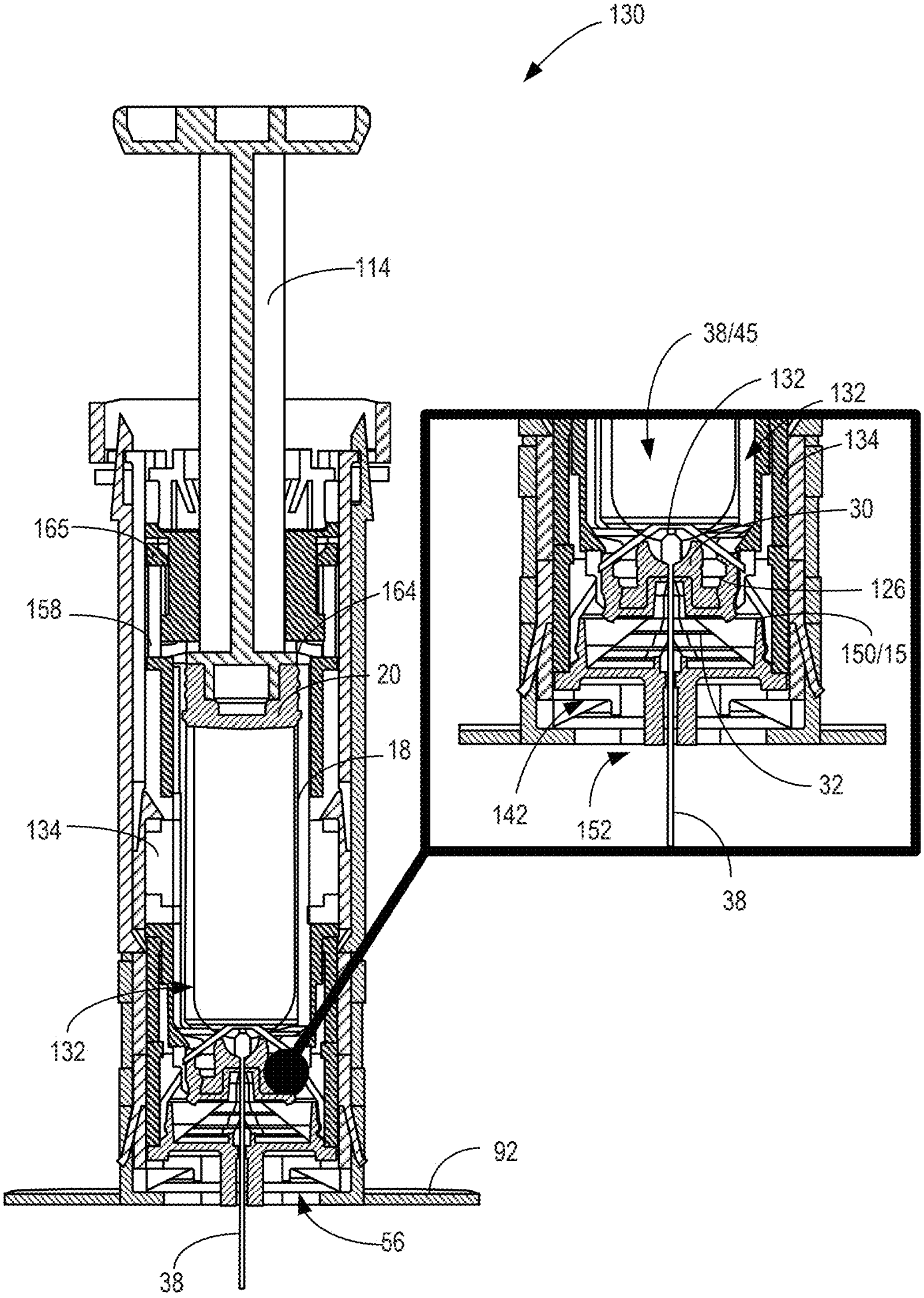

As part of the same initial, distally-directed pressure applied to the plunger rod 114, the container assembly 132 may be caused to move proximally within inner container holder 134, in order to place the needle 38 in fluid communication with the container 18, as shown in FIG. 9C. That is, as the needle 38 is inserted into the patient during application of the initial, distally-directed pressure to the plunger rod 114, a proximal lip or flange 164 of the container 18 is pushed past s retaining member 165 formed at the proximal end of the tube-shaped body 158 of inner container holder 134. With the container assembly 132 moved proximally within inner container holder 134, the protective cap 26 and septum 30 are moved into contact with the fluid transfer assembly 142. Specifically, the protective cap 26 and septum 30 are pushed into the flexible sleeve 154 of valve assembly 150, which deflects/deforms the flexible sleeve 154. As the protective cap 26 and septum 30 are advanced further distally, the proximal sharp end 45 of needle 38 in needle assembly 152 is brought into contact with the pierceable membrane 32 and the septum 30, with the proximal end 45 of the needle 38 being caused to be driven through the pierceable membrane 32 and through the septum 30, so as to place the needle in fluid communication with the inner volume of container 18.

Figure 9D:
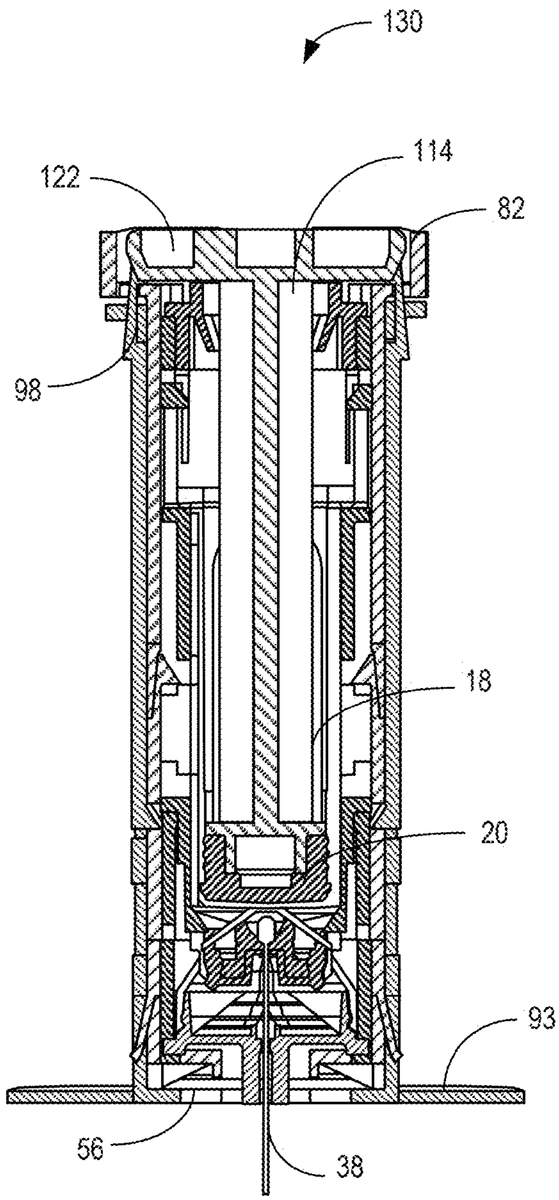

As shown in FIG. 9D, upon placing of the needle 38 in fluid communication with the container 18, a continued distally-directed pressure may be applied to the plunger rod 114 by a user, to force the medicament out from the container 18 and through the needle 38, for administering to the patient. That is, the user may continue to advance the plunger rod 114 and stopper 20 distally into the container 18, thereby forcing the medicament out from the container 18 and through the needle 38.

Figure 9E:
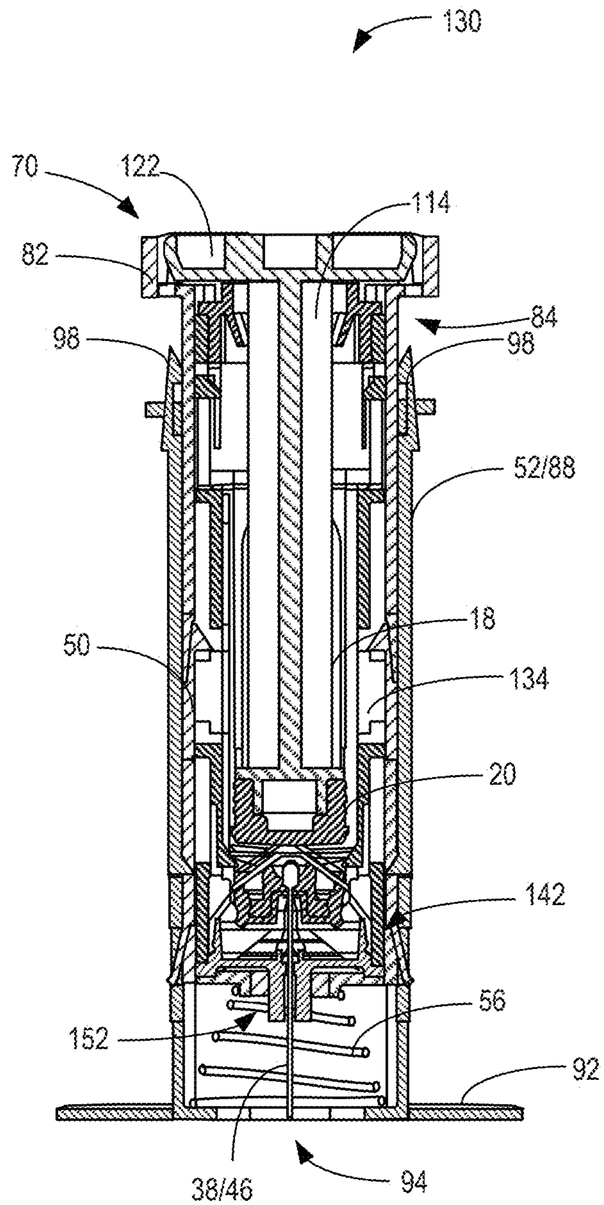
Figure 10:
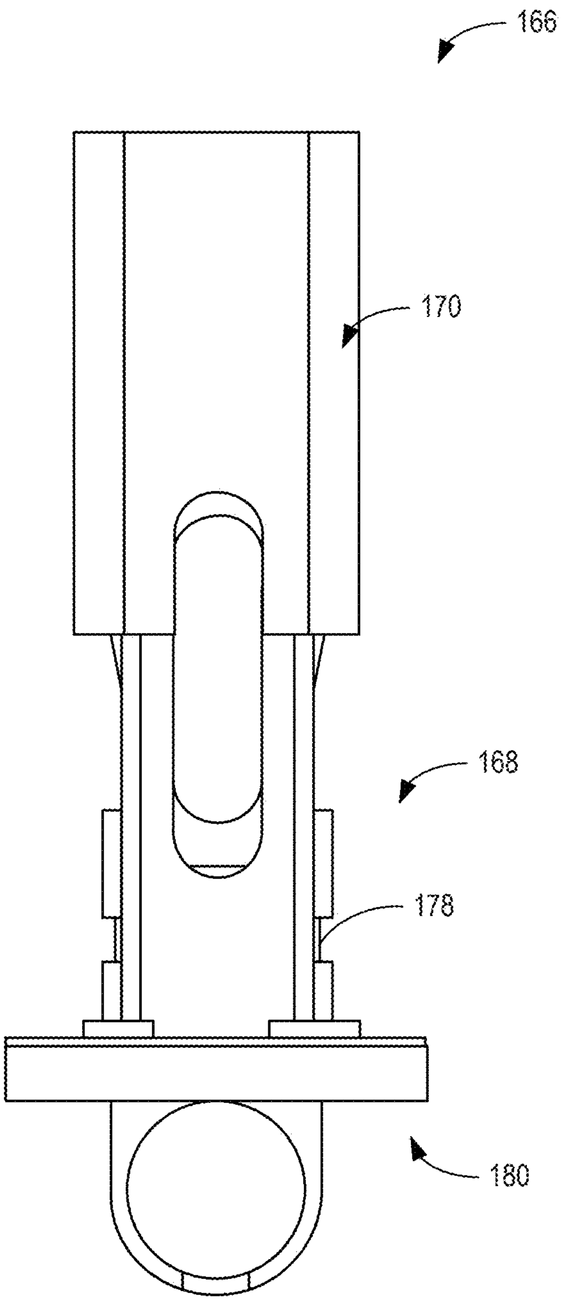
FIG. 10 is a perspective view of a 5-10 mL manual safety injector, according to another non-limiting embodiment described herein.
Figure 11:
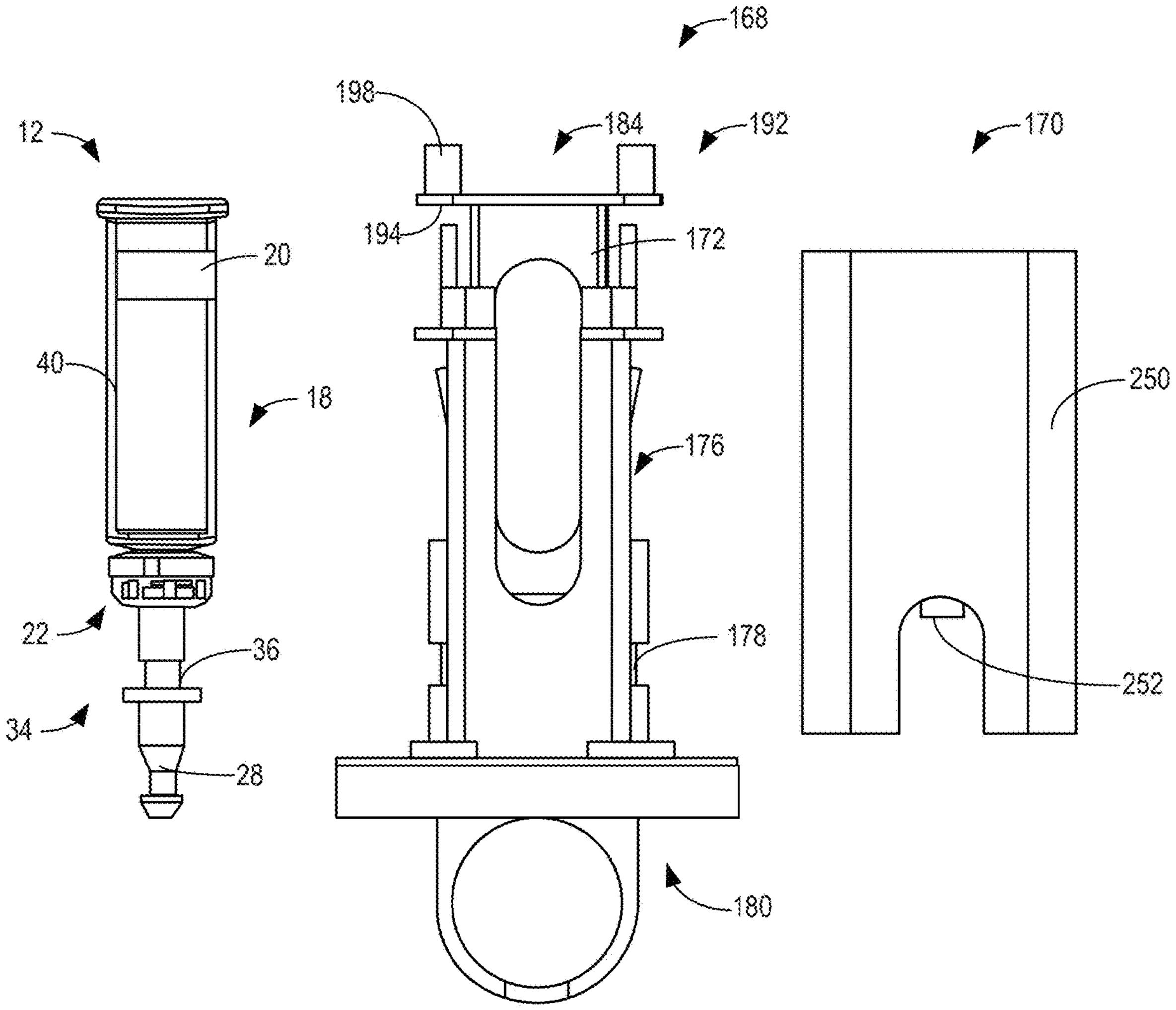
FIG. 11 is an exploded view of the safety injector of FIG. 10 showing a container assembly, injector assembly, and plunger assembly.
Figure 12:
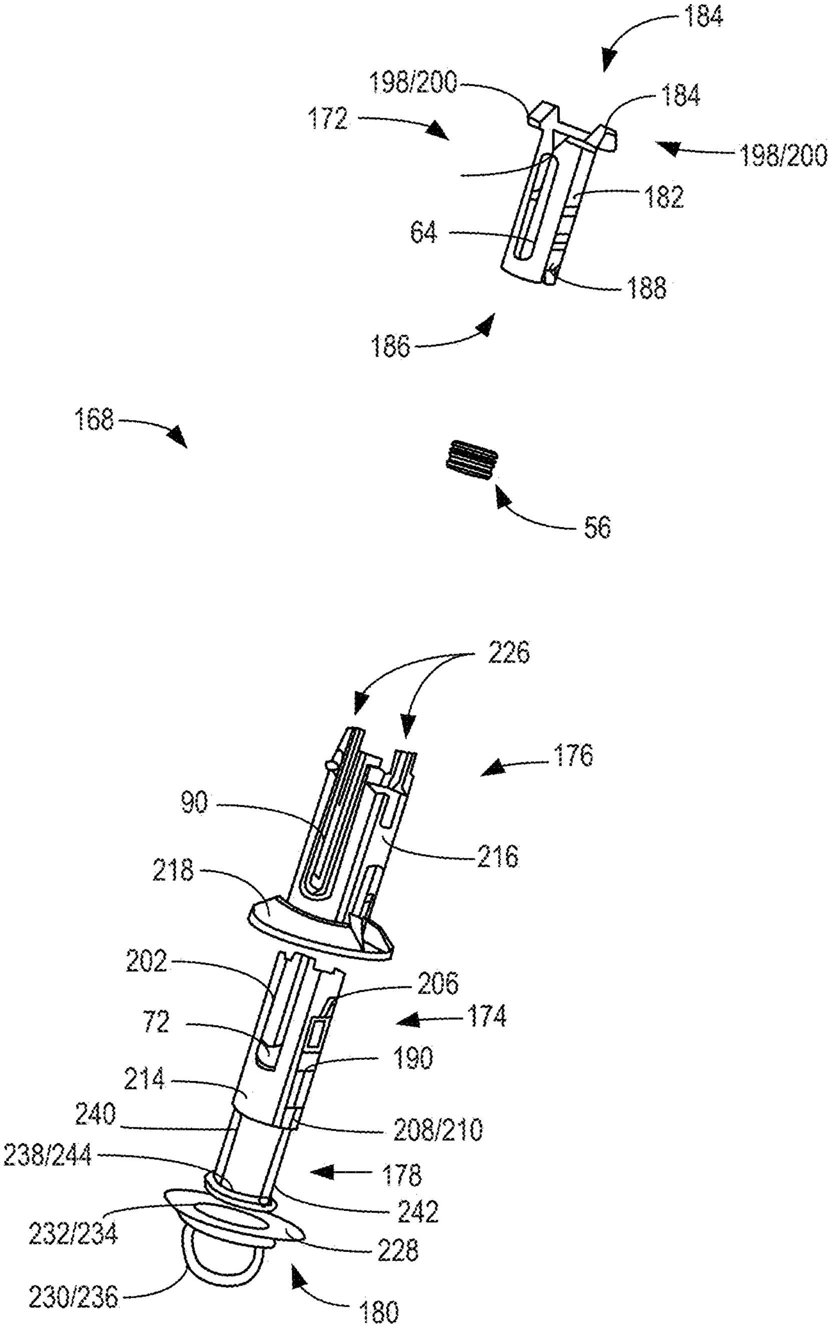
FIG. 12 is an exploded view of the container assembly of FIG. 11.
Figure 13:
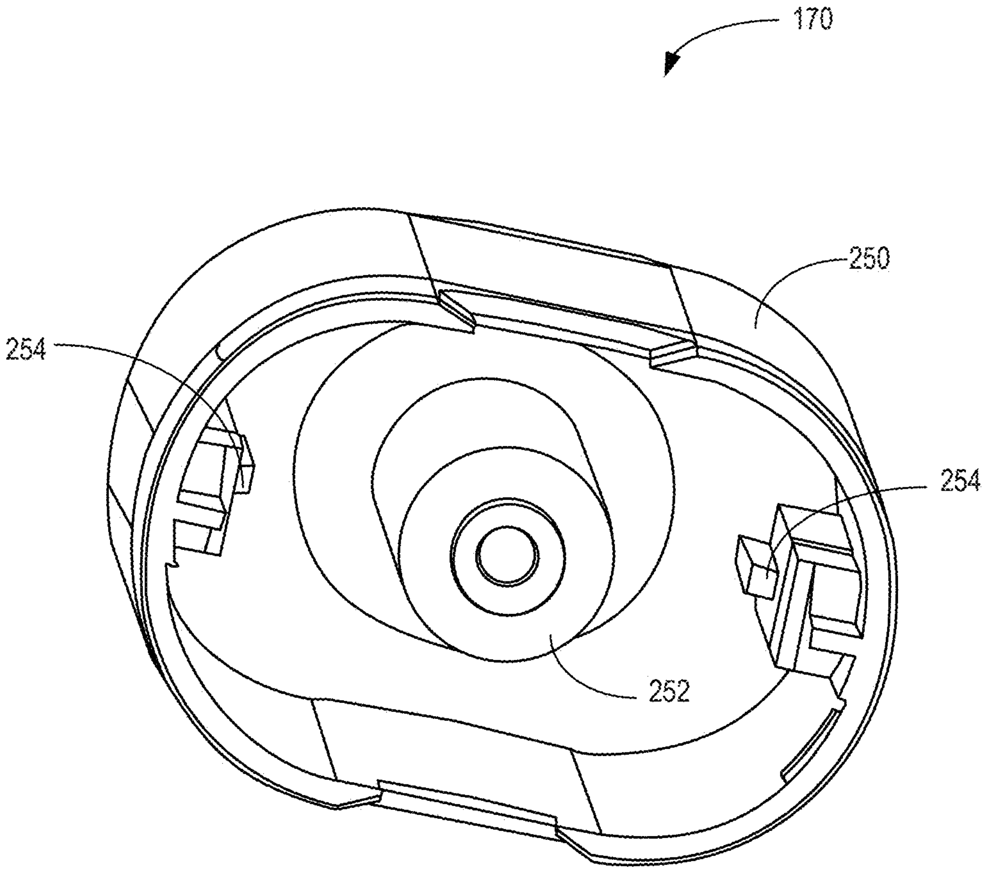
FIG. 13 is an exploded view of the injector assembly of FIG. 11.
Figure 14:
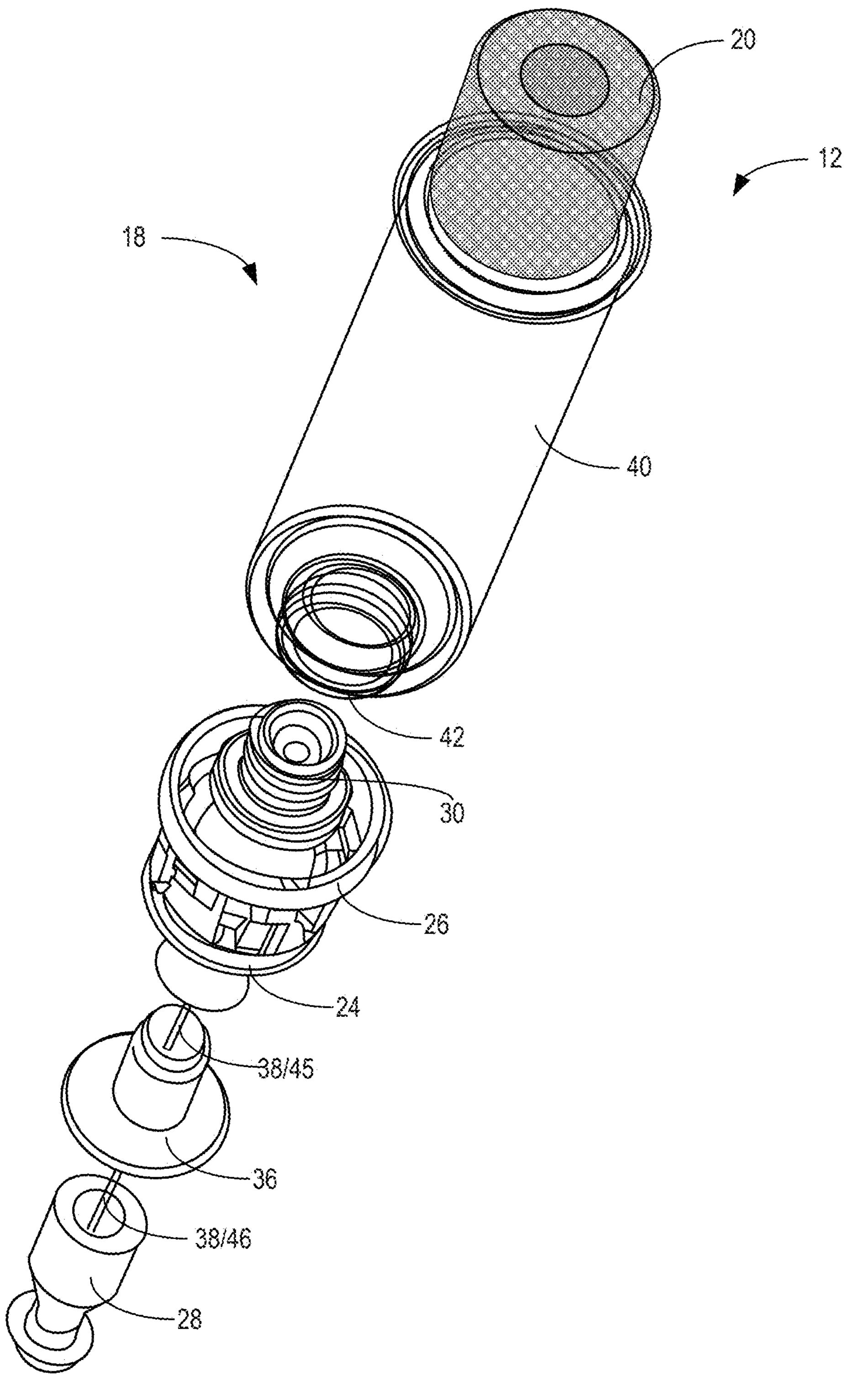
FIG. 14 is an exploded view of the plunger assembly of FIG. 11.

As the plunger rod 114 is approaching being fully depressed into the container 18, a distally-facing surface of the thumb press 122 of the plunger rod 144 is brought into contact with the pair of hook members 98 that extend out in a proximal direction from the holder body 88 of outer holder 52. The thumb press 122 applies a distally directed force to the hook members 98, thereby causing the hook members 98 to become disengaged from the flanged portion 82 of the proximal end member 70 of middle body 50, such that the hook members 98 slide out through the pair of openings 84 formed in the flanged portion 82. With the hook members 98 forced out through the pair of openings 84, the middle body 50 is disengaged from the outer holder 52, thereby allowing for the spring 56 to be released and transition from its compressed state to its extended state. As the spring 56 transitions from its compressed state to its extended state, the middle body 50 is pushed back proximally within the outer holder 52, as shown in FIG. 9E. With the middle body 50 moved back proximally within the outer holder 52, the inner container holder 134—and the fluid transfer assembly 142 (including needle assembly 152) therein—is also caused to move back proximally, such that the needle 38 is retracted from the patient and back into the outer holder 52 (through opening 94 in foot 92). With the needle assembly 152 retracted back proximally, the distal end 46 of the double-ended needle 38 is positioned within the outer holder 52, so as to cover the distal end 46 of the needle 38. Additionally, once the plunger rod is advanced to the fully depressed position, the plunger rod locks, so as to prevent re-use of the safety injector 130.

Referring now to FIGS. 10-15, shown is another non-limiting embodiment of a manually operated/activated safety injector 166 for injecting a 5-10 mL dosage of medicament into a patient. The safety injector 166 may be characterized as generally including a barrel or container assembly 12, an injector assembly 168, and a plunger assembly 170, that may be pre-assembled by a manufacturer prior to receipt and use by a patient or other end user.

Regarding the container assembly 12, the container assembly 12 is structured identically to the container assembly 12 previously described in the safety injector 10 of FIGS. 1-6. Accordingly, the container assembly 12 is not described in detail again herein but, as previously described, generally includes a container 18 (i.e., cartridge or barrel) with a stopper 20 positioned and retained therein, a cap assembly 22 comprising a tip cap needle holder 24 and a protective cap 26, a needle cap 28, a septum 30, a pierceable membrane 32, and a needle assembly 34 comprising a hub 36 and a double-ended needle 38. The container 18 may be provided as a pre-filled cartridge or barrel that contains a volume of medicament or other fluid therein. As described above, the container 18 may contain a medicament or other fluid therein in the amount of 5-10 mL, such that the container 18 may be provided as a 5 mL cartridge/barrel, a 7 mL cartridge/barrel, or a 10 mL cartridge/barrel, as non-limiting examples.

The injector assembly 168 includes an inner container holder 172, a middle body 174, an outer holder 176, a skin sensor 178, a safety cap 180, and a biasing member or spring 56.

The inner container holder 172 of the injector assembly 168 may comprise a generally elongated member that is configured to receive and retain the container assembly therein. The inner container holder 172 may comprise a tube-shaped body 182 having an open proximal end 184 and an open distal end 186. The tube-shaped body 182 includes one or more windows 64 therein through which the container 18 may be viewed. The container assembly 12 may be introduced into the inner container holder 172 via the open proximal end 184, and may be advanced distally through the inner container holder 172 until a distal end of the container body 40 abuts a retainer (e.g., retaining clips or arms, extending radially inward from the tube-shaped body) formed near the distal end of the inner container holder 172. The cap assembly 22 and needle assembly 34 may then protrude distally out past the inner container holder 172.

The tube-shaped body 182 of inner container holder 172 may also include a pair of flexible retention tabs 188 formed at the distal end thereof. The pair of flexible retention tabs 188 extend/angle radially outward from the tube-shaped body 182 and function to engage openings 190 formed in the middle body 174, in order to initially retain the inner container holder 172 in position relative to the middle body 174.

At the proximal end of tube-shaped body 182 is a proximal end member 192 that defines that the open proximal end 184. The proximal end member 192 comprises a flanged portion 194 that extends radially outward from the tube-shaped body 182. The flanged portion 194 may be configured as an oblong flange having a length greater than a width thereof, with the flanged portion 194 including a notch formed therein at each of the opposing lengthwise ends. At each of the lengthwise ends, and on opposing sides of each notch, a pair of extensions 198 is formed that extends up proximally from the flanged portion 194. At each end of the flanged portion 194, the extensions 198 are angled inwardly toward each other, with a proximal end of the extensions 198 being separated from one another by a gap—with this gap between the extensions 198 functioning as a guide channel 200 that guides a distal movement of the plunger assembly 170 relative to the inner container holder 172 and middle body 174, as explained in further detail below.

The middle body 174 of the injector assembly 168 is positioned about the inner container holder 172 and receives the inner container holder 172 therein. The inner container holder 172 is received with the middle body 174 so as translatable therein in the longitudinal direction. The middle body 174 may generally comprise a sidewall structure 202 and a distal end member 204.

The sidewall structure 202 includes one or more windows 72 therein through which the container 18 may be viewed, with the window(s) 72 of the middle body 174 aligned with the window(s) 64 of the inner container holder 172. Additionally, a plurality of flexible/bendable tabs may be formed on the sidewall structure 202. A pair of release tabs 206 may be angled radially outward (relative to a remainder of the sidewall structure 202) and function to selectively engage the outer holder 176, to selectively allow or inhibit movement of the middle body 174 relative to the outer holder 176. A plurality of guide tabs 208 may be positioned at the distal end of sidewall structure 202 and angled radially outward (relative to a remainder of the sidewall structure 202), with a pair of guide tabs 208 provided on each of opposing sides of the sidewall structure 202 that are circumferentially spaced apart to function as guide grooves 210 within which the skin sensor 178 may slide, to move relative to the middle body 174.

The distal end member 204 of middle body 174 partially encloses the distal end of the middle body 174, but includes an opening 212 formed therein. The opening 212 in distal end member 204 accommodates positioning of the needle cap 28 therein, and allows for the needle assembly 34 to extend/protrude therethrough when the inner container holder 172 is moved distally through the middle body 174, as explained in further detail below.

In some embodiments, the sidewall structure 202 may include a visual indicator 214 thereon that may indicate to a user when delivery of the medicament within container 18 is complete. The visual indicator 214 may be in the form of a brightly colored line or symbol, for example, that is provided on the sidewall structure 202 near distal end member 204—with the visual indicator 214 becoming visible to the user upon a full depressing of the plunger assembly 170 and a movement of the middle body 174 relative to the outer holder 176, as explained in further detail below.

The outer holder 176 of the injector assembly 168 has a holder body 216 sized to receive the middle body 174 therein. Similar to the middle body 174 and the inner container holder 172, the holder body 216 of outer holder 176 includes one or more windows 90 therein through which the container 18 may be viewed, with the window(s) 90 of the outer holder 176 aligned with the window(s) 72, 64 of the middle body 174 and the inner container holder 172.

A foot 218 is provided on the outer holder 176 at the distal end of the holder body 216. The foot 218 may comprise a circular member that extends radially outward past the holder body 216. The foot 218 may substantially close the distal end of the holder body 216, but includes a needle opening 220 therein that accommodates positioning of the needle cap 28 therein, and allows for the needle 38 to extend/protrude therethrough when the inner container holder 172 is moved distally through the middle body 174, as explained in further detail below. Additionally, the foot 218 may include a pair of arm holes 222 formed on opposing sides of the needle opening 220. The arm holes 222 are arranged and sized to accommodate positioning of arms of skin sensor 178 therethrough, to allow for movement of the skin sensor 178 relative to the outer holder 176, as explained in further detail below.

A distal-facing surface of the foot 218 may comprise a generally flat surface and may be configured as a textured surface having a plurality of ribs—with the distal-facing surface configured to accommodate placement of the safety injector 166 against the skin of a patient when in use. However, a depression 224 may be formed in a central region of the distal-facing surface that is sized and configured to receive a portion of the skin sensor 178 therein, as explained further below. According to embodiments, the distal-facing surface may comprise an adhesive patch 96 that covers a portion or all of the distal-facing surface. The adhesive patch 96 allows for the safety injector 166 to be secured to the skin of a patient, providing improved stability of the injector during use.

The proximal end of the holder body 216 includes a plurality of guide fingers 226 formed thereon that extend out proximally from the holder body 216. A pair of guide fingers 226 is provided on each of opposing sides of the holder body 216 at the proximal end thereof, with the guide fingers 226 being circumferentially spaced apart to form tracks or grooves that guide movement of the plunger assembly 170 relative to the injector assembly 168, and provide a track within which features of the plunger assembly 170 may slide when the plunger assembly 170 is moved distally relative to the injector assembly 168.

The safety cap 180 of the injector assembly 168 is affixed to the foot 218 and includes a cover 228, a pull tab 230, and an arrangement of receptacles 232, 234 formed in a portion of the cover 228. The cover 228 of safety cap 180 has a surface area identical to the foot 218 and is configured to lay flat on and completely cover the foot 218 when positioned thereover. The pull tab 230 may be configured to extend out distally from the cover 228, with the pull tab 230 including a grip 236 with which the finger of a patient may be engaged, to provide for pulling of the safety cap 180 off from the outer holder 176. The receptacles 232, 234 of safety cap 180 are provided as a pair of concentric receptacles that extend out proximally from the pull tab 230, with the receptacles 232, 234 open on the proximal facing surface of the safety cap 180. A first larger receptacle 232 is sized and arranged to accommodate positioning of a portion of skin sensor 178 therein, when the skin sensor 178 is in an initial position where it protrudes out distally past outer holder 176. A second smaller receptacle 234 is positioned within the first receptacle 232 and is sized and arranged to receive the needle cap 28 therein. When a user pulls the pull tab 230 distally away from the outer holder 176, the safety cap 180 may be separated from the foot 218, while the needle cap 28 is retained within the second receptacle 234, allowing for the needle cap 28 to be removed from over the needle 38 in conjunction with removal of the safety cap 180. Removal of the safety cap 180 from the outer holder 176 in this manner thus uncovers the adhesive patch 96 on foot 218 and also uncovers the needle 38, to allow for a subsequent injection to be performed.

According to aspects of the disclosure, the skin sensor 178 of injector assembly 168 is constructed as a U-shaped slide member that includes a cross-bracket 238, a first sliding arm 240, and a second sliding arm 242. The skin sensor 178 may be retained by/between the middle body 174 and the outer holder 176, with the skin sensor 178 extending out distally past the distal outer holder 176. As explained in further detail below, the skin sensor 178 may be pushed back proximally into the outer holder 176 upon the safety injector 166 being applied to the skin of a patient, thereby allowing for insertion of the distal tip 46 of needle 38 into the patient.

A needle opening 244 is formed in the cross-bracket 238, at a central location thereon. The needle opening 244 is sized to receive the needle cap 28 and the needle 38 therein, with the needle opening 244 allowing the needle cap 28 to be removed from injector assembly 168 and allowing the needle 38 to be advanced distally through the needle opening 244 when an injection is to be performed.

The first and second sliding arms 240, 242 are positioned at opposing ends of the cross-bracket 238 and extend back proximally therefrom, with the first and second sliding arms 240, 242 configured to slide through the arm holes 222 formed in foot 218. Each of the sliding arms 240, 242 may be retained between a respective pair of guide tabs 208 formed on the sidewall structure 202 of middle body 174, with the sliding arms 240, 242 able to slide within the guide grooves defined by the guide tabs 208, so that the skin sensor 178 may move relative to the middle body 174. Each of the sliding arms 240, 242 may include a hook 246 at the proximal end thereof. The hooks 246 on sliding arms 240, 242 may be retained within a slot 248 formed in the holder body 216, with the hooks 246 preventing disconnection of the skin sensor 178 from the outer holder 176.

As best shown in FIGS. 15A-15E, the spring 56 of injector assembly 168 is retained between the middle body 174 and the outer holder 176. Specifically, the spring 56 is retained between a distal-facing surface of middle body 174 (i.e., on a distal-facing surface of distal end member 204) and a proximal-facing surface of foot 218. With the safety injector 166 in an initial configuration (prior to any actuation thereof), the spring 56 is retained in a compressed state. As explained in further detail below, the spring 56 may actuate from the compressed state to an extended (or partially extended) state upon completion of an injection, so as to force middle body 174 back proximally within outer holder 176 and thereby provide shielding to the needle 38 after completion of the injection.

The plunger assembly 170 of safety injector 166 is provided as an over-sized component that may be easily gripped and actuated by a user. The plunger assembly 170 generally includes an outer grip 250 having an open distal end and a closed proximal end and that defines an inner chamber, along with a plunger rod or shaft 252 that is positioned within the inner chamber—with the plunger shaft 252 coupled to an inner surface of the outer grip 250 at the closed proximal end and extending distally therefrom. The plunger assembly 170 is configured to receive at least portions of the container assembly 12 and the injector assembly 168 therein—with the plunger assembly 170 configured to be advanced/pushed distally by a user to perform the injection with safety injector 166.

The outer grip 250 of plunger assembly 170 includes guide features 254 on an inner surface thereof that interact with the middle body 174 and outer holder 176, to provide for a distal advancement of the plunger assembly 170. Specifically, longitudinally oriented rails 254 may be formed on the inner surface of grip 250 on each of opposing sides thereof, with the rails 254 configured to engage the guide channels 200 formed by extensions 198 on the proximal end of inner container holder 172 and to engage the tracks formed by guide fingers 226 on the proximal end of outer holder 176—thereby properly aligning the plunger assembly 170 with the injector assembly 168 and providing for a distal advancement of the plunger assembly 170 (i.e., advancement of outer grip 250 down onto and over the middle body 174 and outer holder 176).

The plunger shaft 252 may include a plunger shaft proximal end joined to the inner surface of the outer grip 250 and a plunger shaft distal end. The plunger shaft distal end is configured to mate with the stopper 20 positioned in container 18 and, in some embodiments, may include a flanged extension that engages a cavity formed in the stopper 20. With the plunger shaft distal end mated with the stopper 20, the stopper 20 may be pushed into container 18 upon advancement of the plunger assembly 170, to cause fluid to be expelled from the container 18.

Referring now to FIGS. 15A-15E, operation of the safety injector 166 is described in more detail. As indicated above, the safety injector 166 is pre-assembled by a manufacture, so as to be provided to a user in a ready to use condition.

Figure 15A:
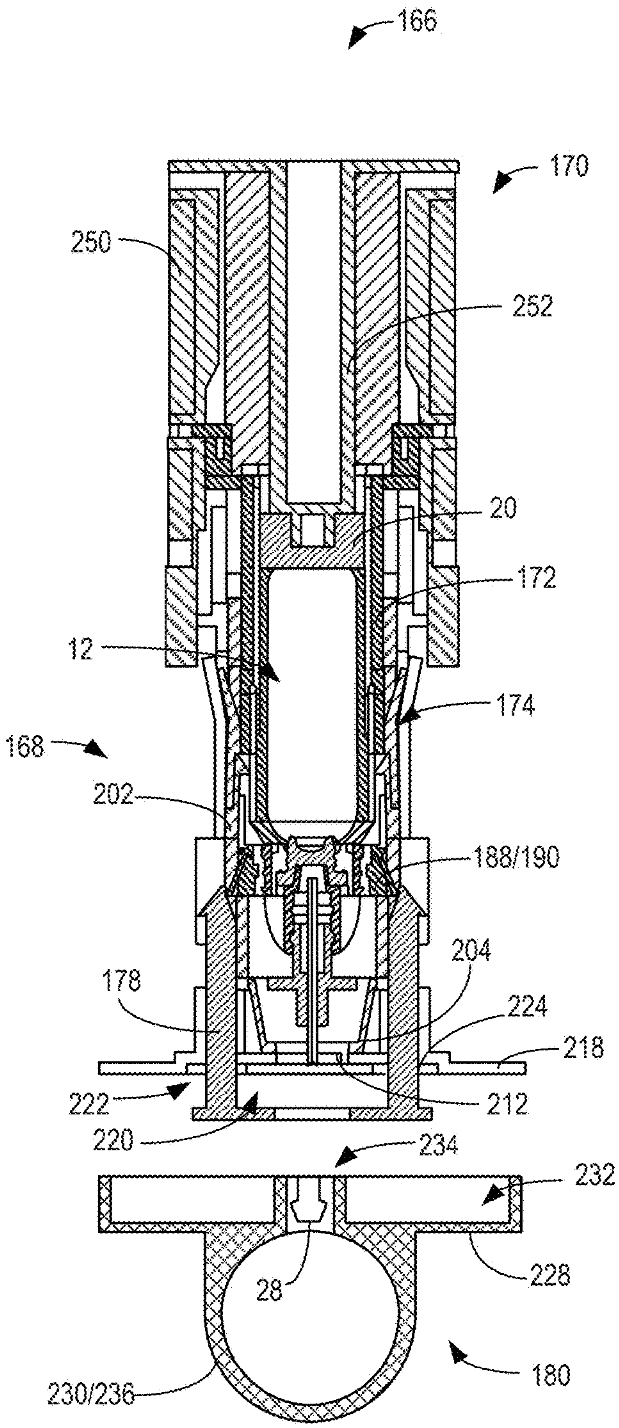
FIGS. 15A-15E are side cross-sectional views of the safety injector of FIG. 10, with the safety injector in different operational states.

From an initial configuration of the safety injector 166, as shown in FIG. 15A, a user will first remove the safety cap 180 and needle cap 28 from the injector. Removal of the safety cap 180 uncovers the adhesive patch 96 on the distally facing surface of the foot 218, along with exposing the skin sensor 178.

Figure 15B:
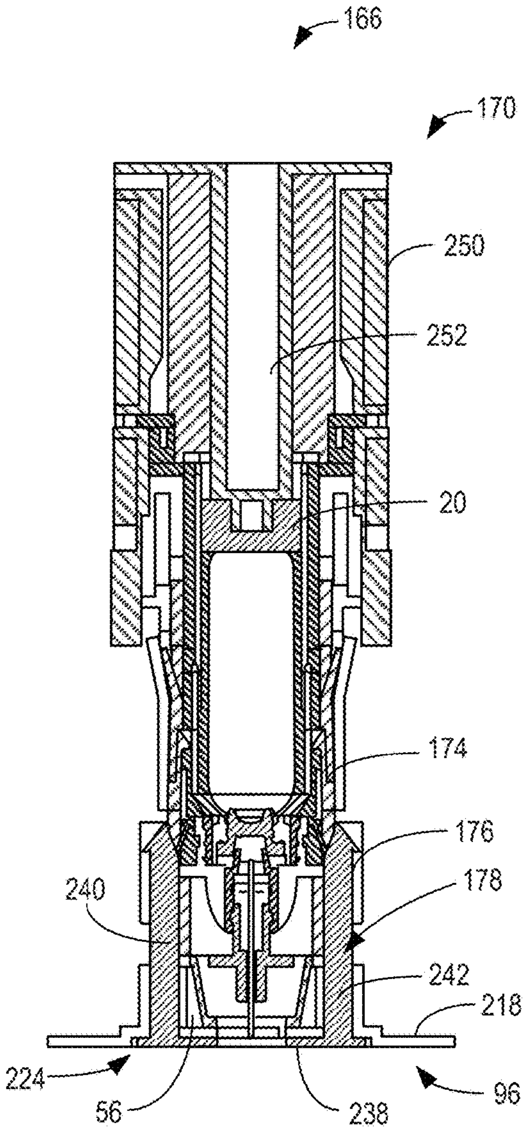

With the safety cap 180 and needle cap 28 removed from the safety injector 166, the safety injector 166 may be adhered to the skin of the patient. As the safety injector 166 is adhered to the skin, the skin sensor 178 is pushed into contact with the skin, thus causing the skin sensor 178 to be depressed proximally back into the outer holder 176, with the sliding arms 240, 242 of the skin sensor 178 sliding proximally relative to the middle body 174 and outer holder 176 and the cross-bracket 238 pushed back into the depression 224 formed in the distal-facing surface of foot 218, as shown in FIG. 15B.

Figure 15C:
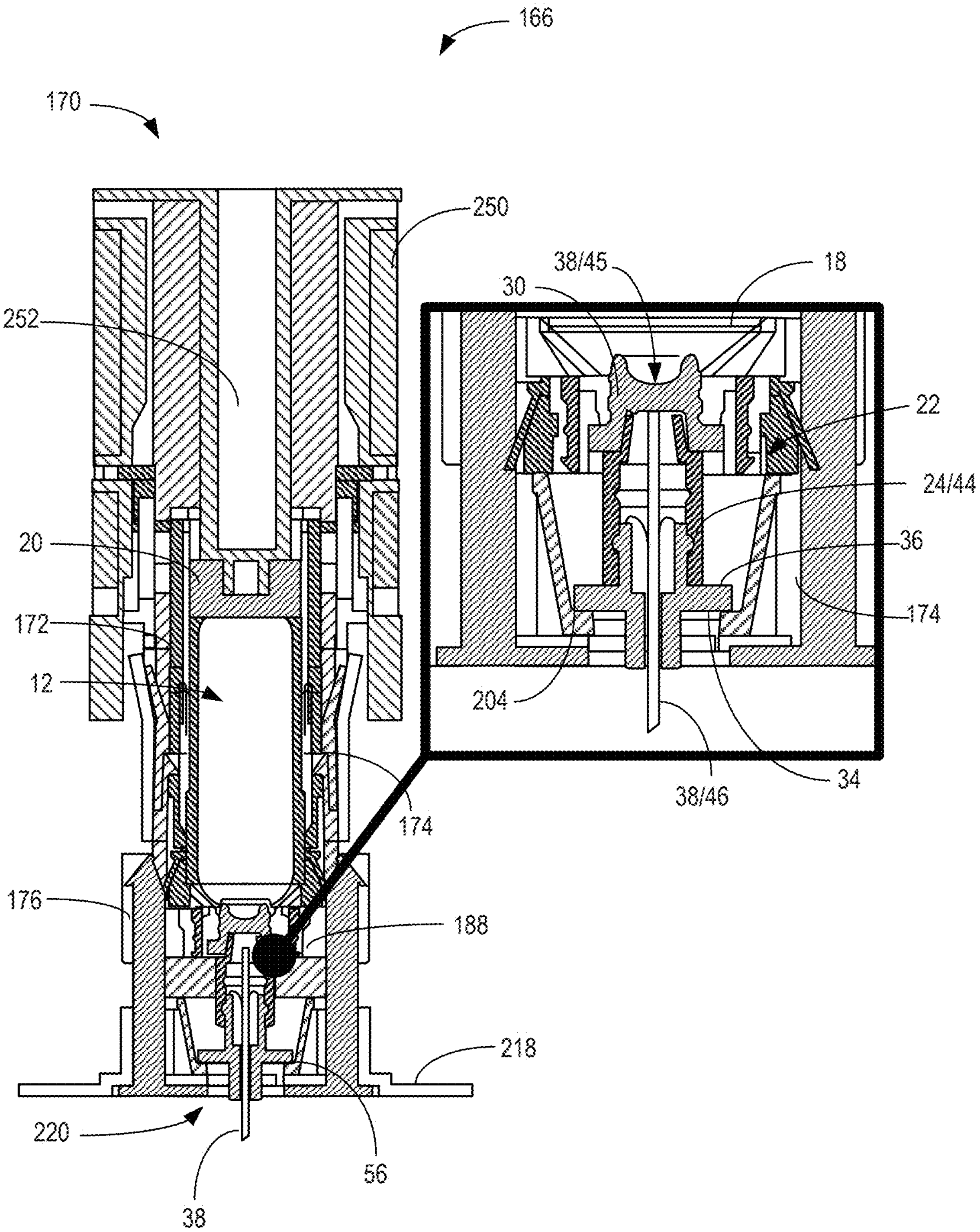

Upon activation/depression of the skin sensor 178, the needle 38 may then be inserted into the patient, as shown in FIG. 15C. Insertion of the needle 38 is achieved by application of an initial, distally-directed pressure to the outer grip 250 of plunger assembly 170, with this pressure causing the inner container holder 172 (and the container assembly 12 retained therein) to move distally further into the middle body 174. Specifically, application of an initial, distally-directed pressure to the outer grip 250 causes the retention tabs 188 at the distal end of the inner container holder 172 to become disengaged from the middle body 174, thereby providing for distal movement of the inner container holder 172 and the container assembly 12 within the middle body 174. With the container assembly 12 (and inner container holder 172) moved distally within the middle body 174, the needle 38 is caused to protrude out distally from the outer holder 176, such that the needle 38 is injected into the patient.

As part of the same initial, distally-directed pressure applied to the plunger assembly 170, the needle assembly 34 may be caused to move proximally relative to cap assembly 22, in order to place the needle 38 in fluid communication with the container 18, as further shown in FIG. 15C. That is, as the needle 38 is inserted into the patient during application of the initial, distally-directed pressure to the plunger assembly 170, the hub 36 of needle assembly 34 comes into contact with the distal end member 204 of middle body 174, such that the continued application of a distally-directed pressure to the plunger assembly 170 causes the hub 36 to be pushed back proximally further into the annular seat 44 of the tip cap needle holder 24. As the hub 36 is pushed proximally back into the tip cap needle holder 24, the proximal end 45 of the needle 38 is caused to be driven through the septum 30, so as to place the needle 38 in fluid communication with the inner volume of container 18.

Figure 15D:
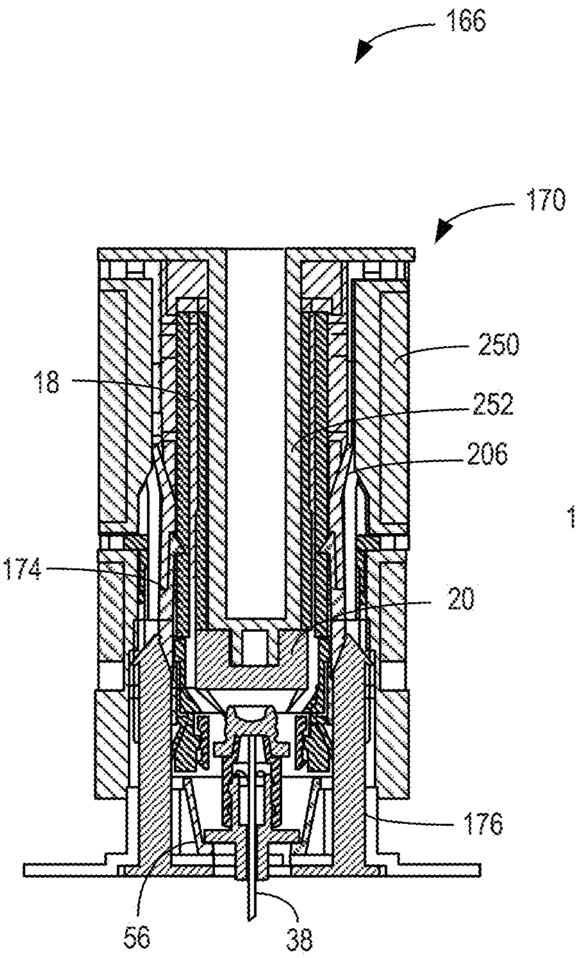

As shown in FIG. 15D, upon placing of the needle 38 in fluid communication with the container 18, a continued distally-directed pressure may be applied to the plunger assembly 170 by a user (via outer grip 250), to force the plunger shaft 252 through the container 18 and expel the medicament out from the container 18 and through the needle 38, for administering to the patient. That is, the user may continue to advance the plunger shaft 252 and stopper 20 distally into the container 18 via actuation of the outer grip 250, thereby forcing the medicament out from the container 18 and through the needle 38.

Figure 15E:
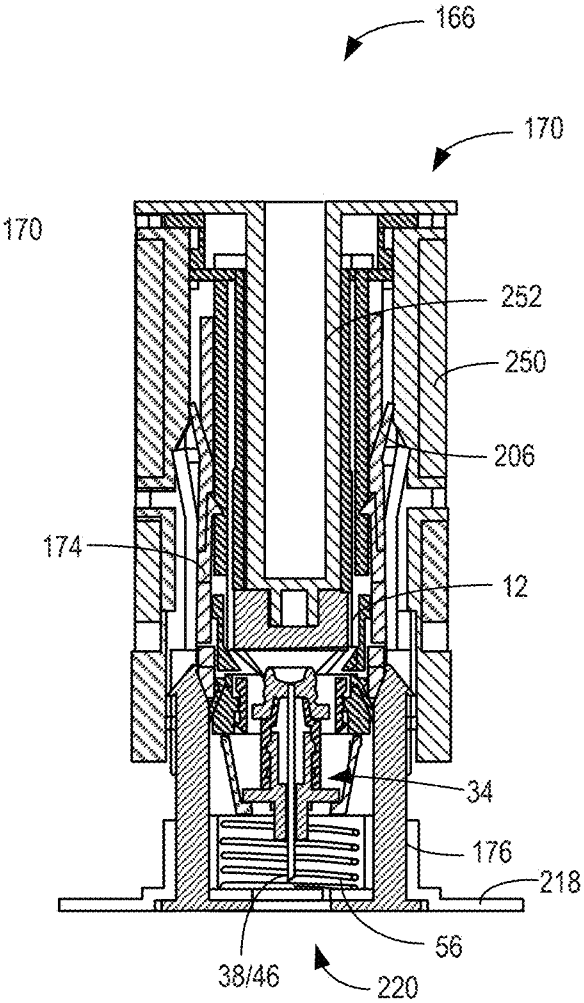

As the plunger assembly 170 approaches being fully depressed, internal features provided on the inner surface of the outer grip 250—i.e., rails 254—interact with the outer holder 176 in order to cause the pair of release tabs 206 on the middle body 174 to deflect inwardly. The inward deflection of the release tabs 206 causes the middle body 174 to become unlocked/disengaged from the outer holder 176, thereby allowing for the spring 56 to be released and transition from its compressed state to its extended state. As the spring 56 transitions from its compressed state to its extended state, the middle body 174 is pushed back proximally within the outer holder 176, as shown in FIG. 15E. With the middle body 174 moved back proximally within the outer holder 176, the container assembly 12—and the needle assembly 34 thereof—is also caused to move back proximally, such that the needle 38 is retracted from the patient and back into the outer holder 176 (through opening 220 in foot 218). With the container assembly 12 and needle assembly 34 retracted back proximally, the distal end 46 of the double-ended needle 38 is positioned within the outer holder 176, so as to cover the distal end 46 of the needle 38.

In some embodiments, the proximal movement of the middle body 174 within the outer holder 176 causes the visual indicator 214 (e.g., colored line or symbol) provided near the distal end of the sidewall structure 202 of the middle body 174 to become visible. The visual indicator 214 (FIG. 12) may thus confirm to the user that the injection of the medicament is complete.

Figure 16:
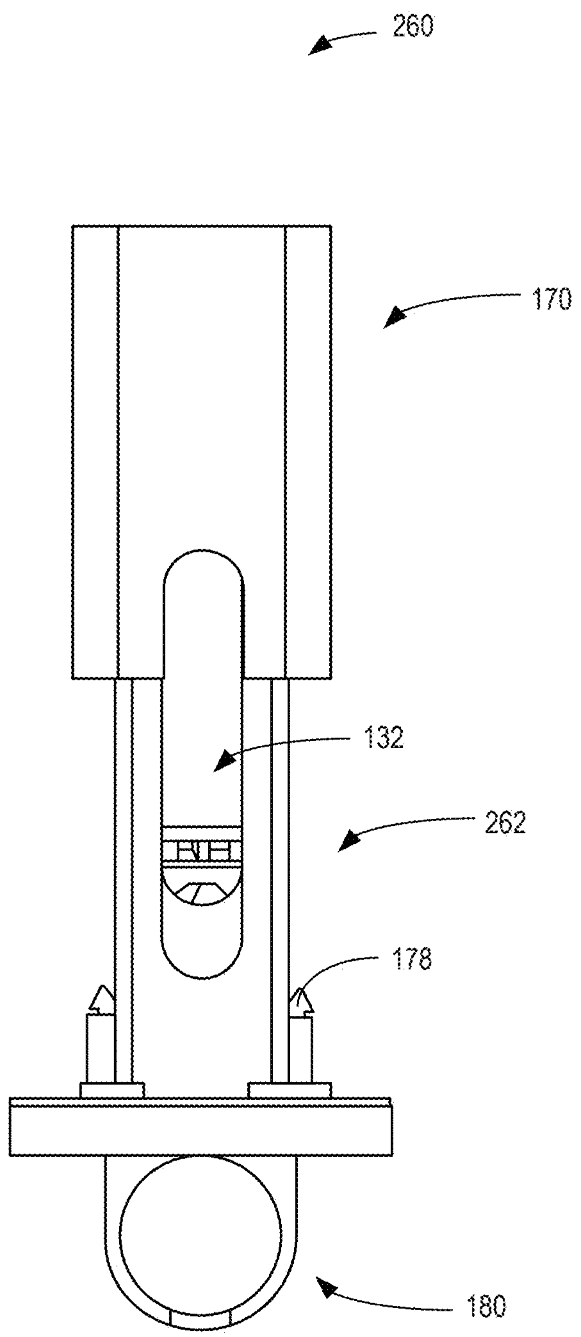
FIG. 16 is a perspective view of a 5-10 mL manual safety injector, according to another non-limiting embodiment described herein.
Figure 17:
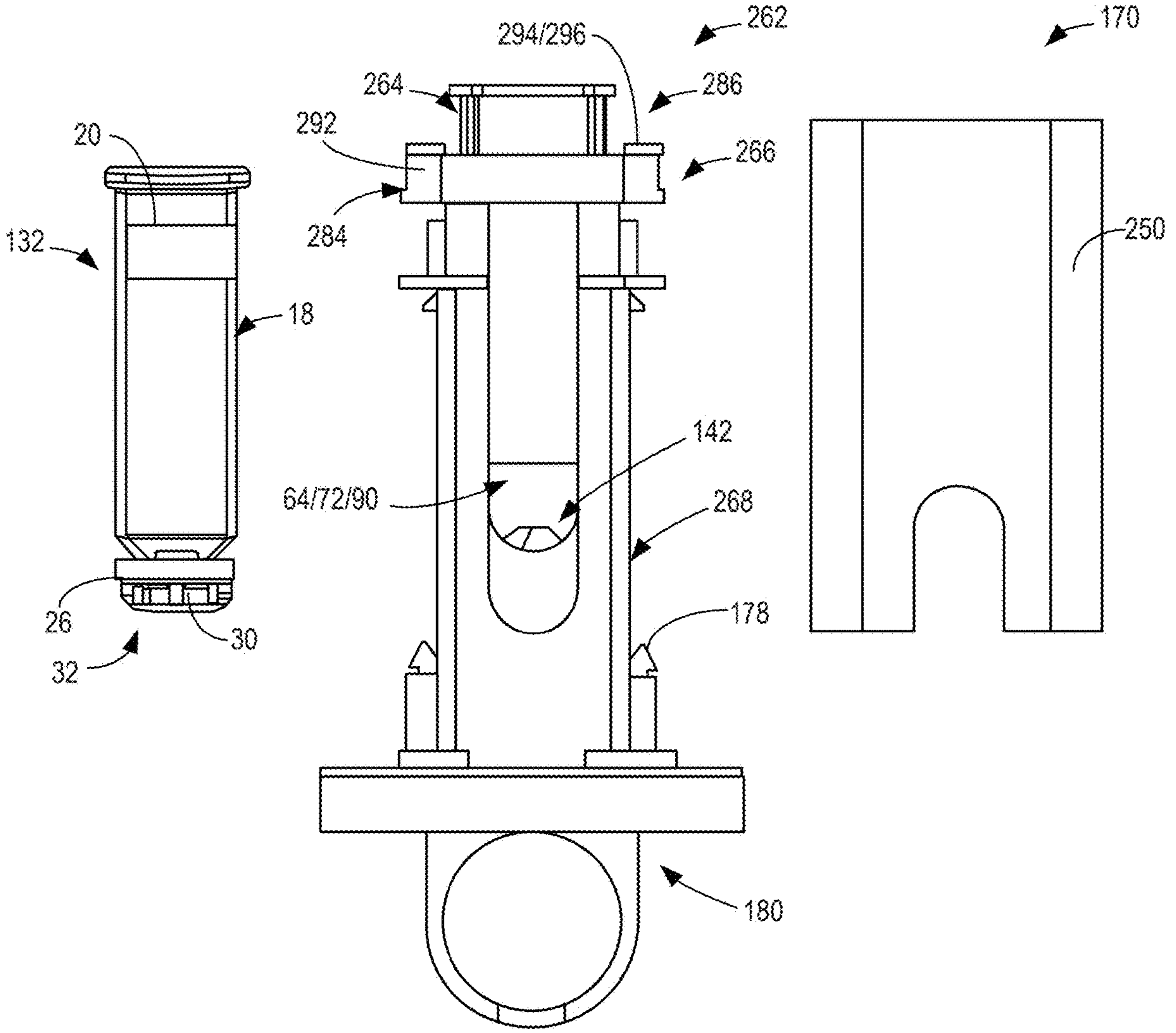
FIG. 17 is an exploded view of the safety injector of FIG. 16 showing a container assembly, injector assembly, and plunger assembly.

Referring now to FIGS. 16-18, shown is another non-limiting embodiment of a manually operated/activated safety injector 260 for injecting a 5-10 mL dosage of medicament into a patient. The safety injector 260 may be characterized as generally including a barrel or container assembly 132, an injector assembly 262, and a plunger assembly 170, that may be pre-assembled by a manufacturer prior to receipt and use by a patient or other end user.

Regarding the container assembly 132, the container assembly 132 is structured identically to the container assembly 132 previously described in the safety injector 130 of FIGS. 7-9. Accordingly, the container assembly 132 is not described in detail again herein but, as previously described, generally includes a container 18 (i.e., a cartridge or barrel) with a stopper 20 positioned and retained therein, a protective cap 26, a septum 30, and a pierceable membrane 32. The container 18 may be provided as a pre-filled cartridge or barrel that contains a volume of medicament or other fluid therein. As described above, the container 18 may contain a medicament or other fluid therein in the amount of 5-10 mL, such that the cartridge may be provided as a 5 mL cartridge/barrel, a 7 mL cartridge/barrel, or a 10 mL cartridge/barrel, as non-limiting examples.

The injector assembly 262 includes an inner container holder 264, a middle body 266, an outer holder 268, a safety cap 180, a skin sensor 178, a fluid transfer assembly 142, and a biasing member or spring 56. According to embodiments, the safety cap 180 and skin sensor 178 are constructed identically to the safety cap 180 and skin sensor 178 of the safety injector of FIGS. 10-15, while the fluid transfer assembly 142 is constructed identically to the fluid transfer assembly 142 of the safety injector 130 of FIGS. 7-9, and thus reference is made to the previous description of those components and not repeated here, with like numbers used to identify those components in FIGS. 16-18.

The inner container holder 264 of the injector assembly 262 may comprise a generally elongated member that is configured to receive and retain the container assembly 132 therein. The inner container holder 264 may comprise a tube-shaped body 270 having an open proximal end 272 and an open distal end 274. The tube-shaped body 270 includes one or more windows 64 therein through which the container 18 may be viewed. The container assembly 132 may be introduced into the inner container holder 264 via the open proximal end 272, and may be advanced distally through the inner container holder 264 until a proximal lip or flange of the container body 40 abuts a retaining member formed at the proximal end of the tube-shaped body 270, such as a lip or flange 271 formed on the tube-shaped body 270.

The tube-shaped body 270 may further include a plurality of openings 276, 278 formed therein at locations spaced apart longitudinally along a length thereof, with the openings configured to receive release tabs 280 formed on the middle body 266. The plurality of openings may at least include a first pair of openings 276 and a second pair of openings 278, with the second pair of openings 278 located proximally from the first pair of openings 276.

The middle body 266 of the injector assembly 262 may comprise a generally elongated member that is positioned about the inner container holder 264 and receives the inner container holder 264 therein, with the inner container holder 264 received within the middle body 266 so as to be translatable therein in the longitudinal direction. The middle body 266 may generally comprise a sidewall structure 282 and a proximal end member 284.

The sidewall structure 282 may be tube-shaped and include an open proximal end 286 and an open distal end 288. The sidewall structure 282 also includes one or more windows 72 therein through which the container 18 may be viewed, with the window(s) 72 of the middle body 266 aligned with the window(s) 64 of the inner container holder 264. Additionally, a plurality of flexible/bendable tabs may be formed on the sidewall structure 282. A first pair of release tabs 290 may be angled radially outward (relative to a remainder of the sidewall structure 282) and function to selectively engage the outer holder 268, to selectively allow or inhibit movement of the middle body 266 relative to the outer holder 268. A second pair of release tabs 280 may be angled or include protrusions that are directed radially inward (relative to a remainder of the sidewall structure 282) and function to selectively engage the first pair of openings 276 and the second pair of openings 278 of the tube-shaped body 270 of inner container holder 264, to selectively allow or inhibit movement of the inner container holder 264 relative to the middle body 266.

At the proximal end of middle body 266 is a proximal end member 284 that defines the open proximal end 272. The proximal end member 284 comprises a flanged portion 292 that extends radially outward from the sidewall structure 282. The flanged portion 292 may be configured as an oblong flange having a length greater than a width thereof, with the flanged portion 292 including a notch (not shown) formed therein at each of the opposing lengthwise ends. At each of the lengthwise ends, and on opposing sides of each notch, a pair of extensions 294 is formed that extends up proximally from the flanged portion 292. At each end of the flanged portion 292, the extensions 294 are angled inwardly toward each other, with a proximal end of the extensions 294 being separated from one another by a gap—with this gap between the extensions 294 functioning as a guide channel 296 that guides a distal movement of the plunger assembly 170 relative to the inner container holder 264 and middle body 266, as explained in further detail below.

The distal end 274 of sidewall structure 282 is configured to couple with the fluid transfer assembly 142, such as via securing of an outer circumferential edge of the needle shield holder 156 connecting to the sidewall structure 282. With the fluid transfer assembly 142 coupled to the distal end of the sidewall structure 282, the valve assembly 150 may be positioned internally within the sidewall structure 282, while a distal portion of the needle shield holder 156 and the distal end of the needle 38 protrude distally out past the sidewall structure 282 of middle body 266.

With the inner container holder 264 in an initial position relative to middle body 266, the container assembly 132 and the fluid transfer assembly 142 are arranged so as to be spaced apart in the longitudinal direction. That is, a gap is provided between the protective cap 26 and the valve assembly 150 with the inner container holder 264 in an initial position within middle body 266. During use of the safety injector 260, the inner container holder 264 (and container assembly 132) may be caused to move distally within the middle body 266, thereby bringing the container assembly 132 into contact with the fluid transfer assembly 142, as explained in further detail below.

The outer holder 268 of the injector assembly 262 has a holder body 298 sized to receive the middle body 266 therein. Similar to the middle body 266 and the inner container holder 264, the holder body 298 of outer holder 268 includes one or more windows 90 therein through which the container 18 may be viewed, with the window(s) 90 of the outer holder 268 aligned with the window(s) 72, 64 of the middle body 266 and the inner container holder 264. Additionally, the holder body 298 may include a plurality of openings 300, 302 formed therein at locations spaced apart longitudinally along a length thereof, with the openings configured to receive the first pair of release tabs 290 formed on the middle body 266. The plurality of openings may at least include a first pair of openings 300 and a second pair of openings 302, with the second pair of openings 302 located distally from the first pair of openings 300.

The proximal end of the holder body 298 includes a plurality of guide fingers 304 formed thereon that extend out proximally from the holder body 298. A pair of guide fingers 304 is provided on each of opposing sides of the holder body 298 at the proximal end that are circumferentially spaced apart to form tracks or grooves that guide movement of the plunger assembly 170 relative to the injector assembly 262, and provide a track within which features of the plunger assembly 170 may slide when the plunger assembly 170 is moved distally relative to the injector assembly 262.

The distal end of the holder body 298 may include guide channels 306 formed on opposing sides thereof configured to retain the sliding arms 240, 242 of the skin sensor 178. Each of the sliding arms 240, 242 may be retained within a respective guide channel 306 formed on the holder body

298, with the sliding arms 240, 242 able to slide within the guide channels 306, so that the skin sensor 178 may move relative to the outer holder 268.

A foot 218 is provided on the outer holder 268 at the distal end of the holder body 298. The foot 218 may be constructed identical to the foot 218 previously described in the safety injector 166 of FIGS. 10-15, and is thus is not described in detail again herein, but generally includes a needle opening 220, arm holes 222, a depression 224 in a central region of the distal-facing surface thereof, and an adhesive patch 96.

As best shown in FIGS. 18A-18E, the spring 56 of injector assembly 262 is retained between the needle shield holder 156 and the outer holder 268. Specifically, the spring 56 is retained between a distal-facing surface of needle shield holder 156 (within a seat formed on the distal-facing surface) and a proximal-facing surface of foot 218. With the safety injector 260 in an initial configuration (prior to any actuation thereof), the spring 56 is retained in an extended (or partially extended) state. As explained in further detail below, the spring 56 may actuate from the extended state to the compressed state, and then back to the extended (or partially extended) state upon completion of an injection, so as to force middle body 266 back proximally within outer holder 268 and thereby provide shielding to the needle 38 after completion of the injection.

The plunger assembly 170 of safety injector 260 may be constructed similarly/identical to the plunger assembly 170 previously described in the safety injector of FIGS. 10-15, with the plunger assembly 170 including an outer grip 250 having an open distal end and a closed proximal end and that defines an inner chamber, along with a plunger rod or shaft that is positioned within the inner chamber—with the plunger shaft 252 coupled to an inner surface of the outer grip 250 at the closed proximal end and extending distally therefrom. The plunger assembly 170 is configured to receive at least portions of the container assembly 132 and the injector assembly 262 therein—with the plunger assembly 170 configured to be advanced/pushed distally by a user to perform the injection with safety injector 260.

Referring now to FIGS. 18A-18E, operation of the safety injector 260 is described in more detail. As indicated above, the safety injector 260 is pre-assembled by a manufacture, so as to be provided to a user in a ready to use condition.

Figure 18A:
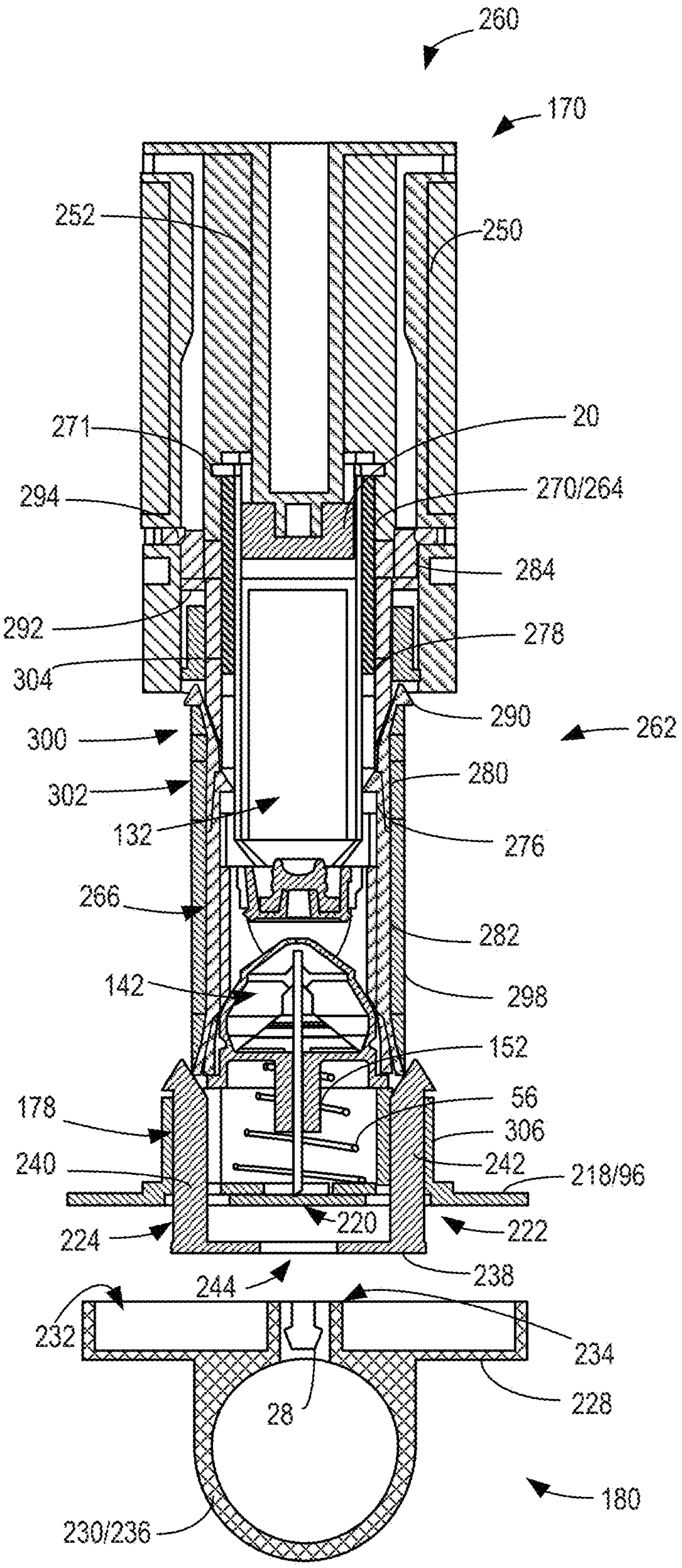
FIGS. 18A-18E are side cross-sectional views of the safety injector of FIG. 16, with the safety injector in different operational states.

From an initial configuration of the safety injector 260, as shown in FIG. 18A, a user will first remove the safety cap 180 and needle cap 28 from the injector. Removal of the safety cap 180 uncovers the adhesive patch 96 on the distally facing surface of the foot 218, along with exposing the skin sensor 178.

With the safety cap 180 and needle cap 28 removed from the safety injector 260, the safety injector 260 may be adhered to the skin of the patient. As the safety injector 260 is adhered to the skin, the skin sensor 178 is pushed into contact with the skin, thus causing the skin sensor 178 to be depressed proximally back into the outer holder 268, with the sliding arms 240, 242 of the skin sensor 178 sliding proximally relative to the outer holder 268 and the cross-bracket 238 pushed back into the depression 224 formed in the distal-facing surface of foot 218, as shown in FIG. 18B.

Figure 18B:
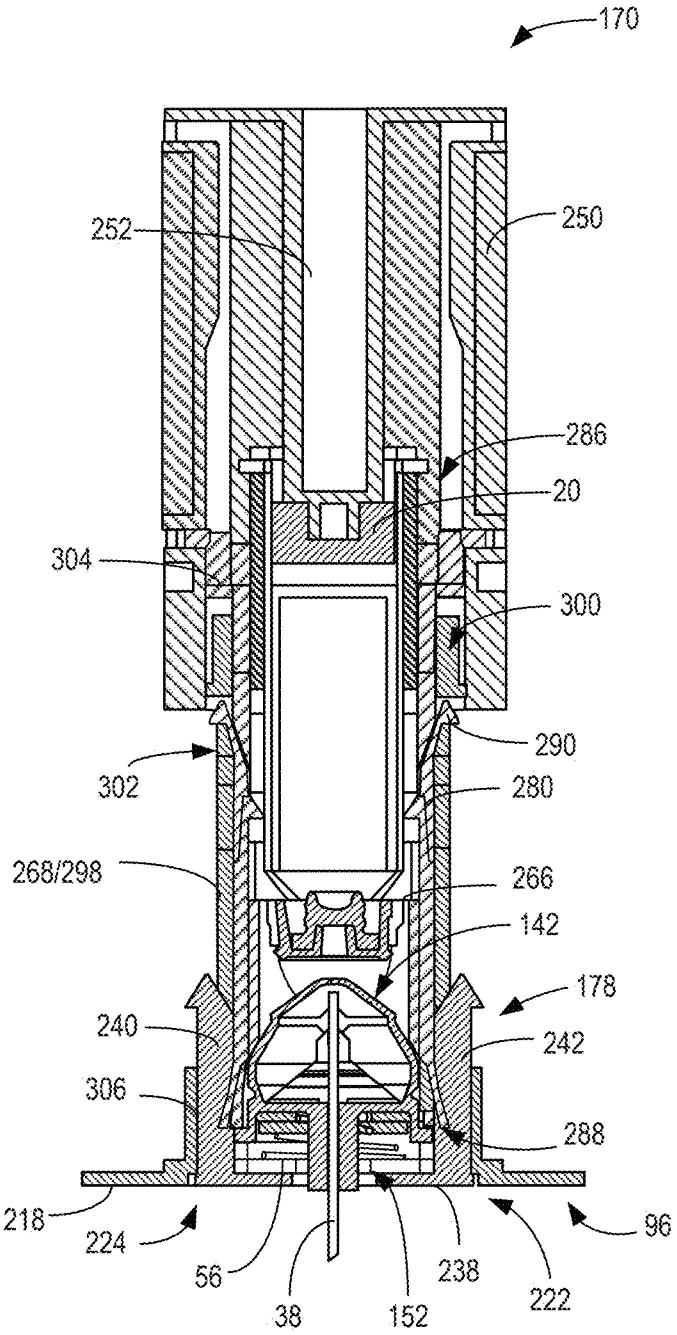

As further shown in FIG. 18B, upon activation/depression of the skin sensor 178, the needle 38 may then be inserted into the patient. Insertion of the needle 38 is achieved by application of an initial, distally-directed pressure to the outer grip 250 of plunger assembly 170, with this pressure causing the middle body 266 to move distally further into the outer holder 268. Specifically, application of an initial, distally-directed pressure to the outer grip 250 causes the first pair of release tabs 290 on middle body 266 to become disengaged from the first pair of openings 300 in holder body 298, thereby providing for distal movement of the middle body 266 within the outer holder 268—with the middle body 266 moving distally until the first pair of release tabs 290 on middle body 266 become engaged with the second pair of openings 302 in holder body 298. With the middle body 266 (and needle assembly 152 retained thereon) moved distally within the outer holder 268, the needle 38 is caused to protrude out distally from the outer holder 268, such that the needle 38 is injected into the patient. Additionally, as the middle body 266 moves distally within the outer holder 268, the spring 56 is caused to transition from its extended state to its compressed state, with the spring 56 then retained in the compressed state due to locking of the first pair of release tabs 290 on middle body 266 within the second pair of openings 302 in holder body 298.

Figure 18C:
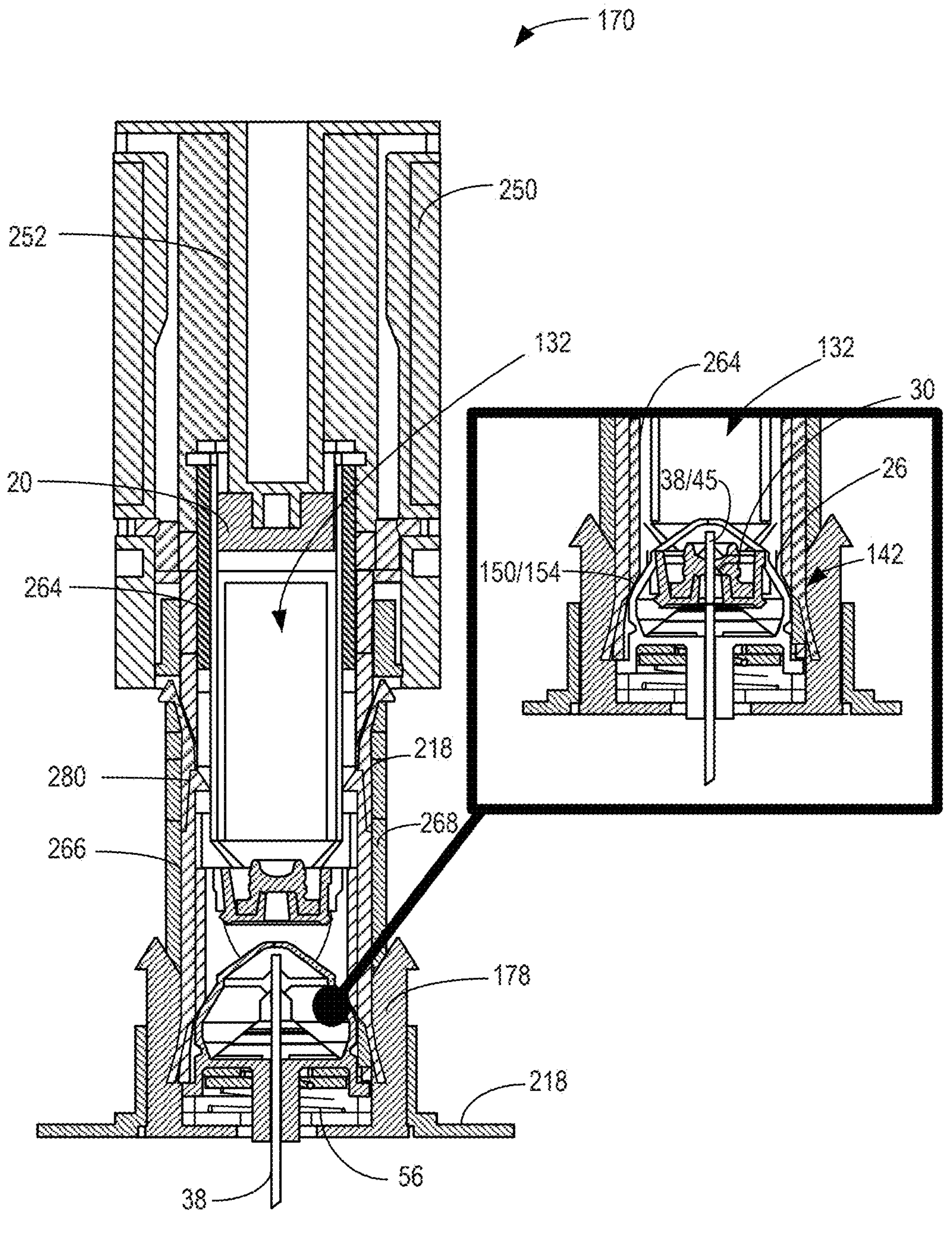

As shown in FIG. 18C, as part of the same initial distally-directed pressure applied to the plunger assembly 170, the inner container holder 264 (and the container assembly 132 retained therein) is caused to move distally further into the middle body 266. Specifically, application of an initial, distally-directed pressure to the outer grip 250 causes the second pair of release tabs 280 on middle body 266 to become disengaged from the first pair of openings 276 in inner container holder 264, thereby providing for distal movement of the inner container holder 264 (and the container assembly 132) within the middle body 266—with the inner container holder 264 moving distally until the second pair of release tabs 280 on middle body 266 become engaged with the second pair of openings 278 in inner container holder 264.

With the inner container holder 264 (and container assembly 132) moved distally within the middle body 266, the protective cap 26 and septum 30 of container assembly 132 are moved into contact with the fluid transfer assembly 142. Specifically, the protective cap 26 and septum 30 are pushed into the flexible sleeve 154 of valve assembly 150, which deflects/deforms the flexible sleeve 154. As the protective cap 26 and septum 30 are advanced further distally, the proximal sharp end 45 of needle 38 in needle assembly 152 is brought into contact with the septum 30, with the proximal end 45 of the needle 38 being caused to be driven through the septum 30, so as to place the needle 38 in fluid communication with the inner volume of container 18.

Figure 18D:
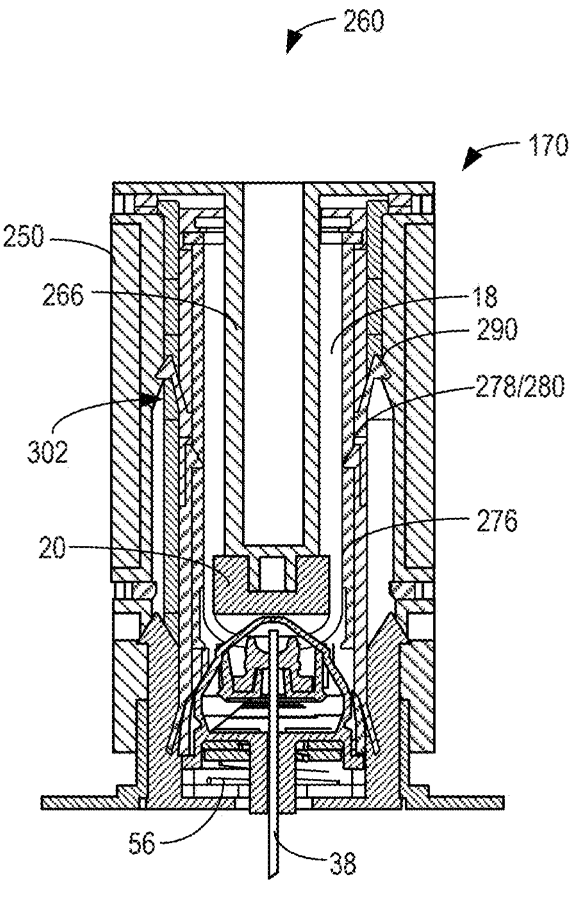

As shown in FIG. 18D, upon placing of the needle 38 in fluid communication with the container 18, a continued distally-directed pressure may be applied to the plunger assembly 170 by a user (via outer grip 250), to force the plunger shaft 252 through the container 18 and expel the medicament out from the container 18 and through the needle 38, for administering to the patient. That is, the user may continue to advance the plunger shaft 252 and stopper 20 distally into the container 18 via actuation of the outer grip 250, thereby forcing the medicament out from the container 18 and through the needle 38.

Figure 18E:
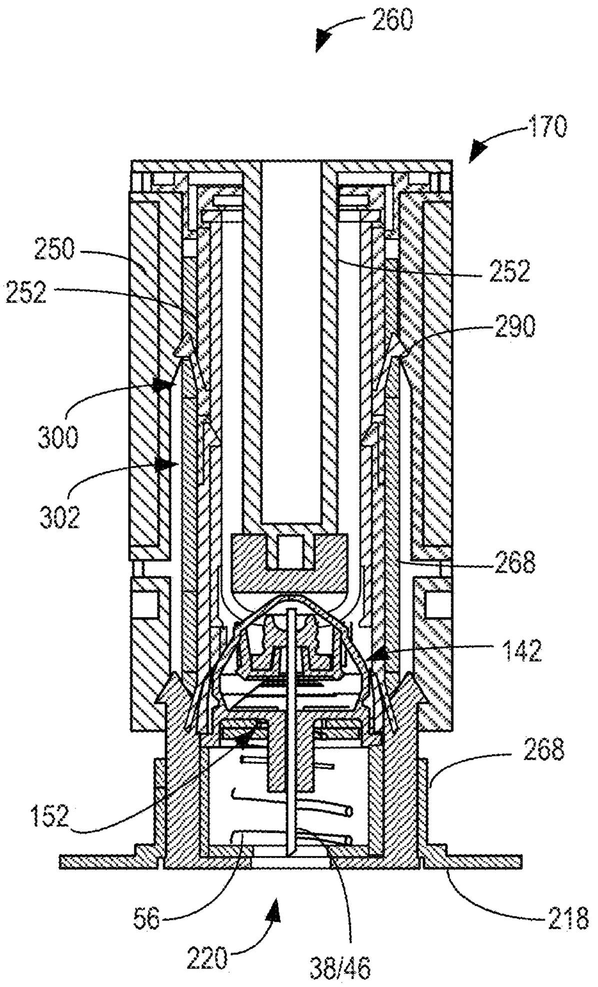

As the plunger assembly 170 approaches being fully depressed, internal features provided on the inner surface of the outer grip 250 interact with the outer holder 268 in order to cause the first pair of release tabs 290 on middle body 266 to deflect inwardly and become disengaged from the second pair of openings 302 in holder body 298. The inward deflection of the first pair of release tabs 290 causes the middle body 266 to become unlocked/disengaged from the outer holder 268, thereby allowing for the spring 56 to be released and transition from its compressed state back to its extended state. As the spring 56 transitions from its compressed state to its extended state, the middle body 266 is pushed back proximally within the outer holder 268, as shown in FIG. 18E, until the first pair of release tabs 290 on middle body 266 become engaged with the first pair of openings 300 in holder body 298. With the middle body 266 moved back proximally within the outer holder 268, the fluid transfer assembly 142—including the needle assembly 152 thereof—is also caused to move back proximally, such that the needle 38 is retracted from the patient and back into the outer holder 268 (through opening 220 in foot 218). With the middle body 266 and needle assembly 152 retracted back proximally, the distal end 46 of the double-ended needle 38 is positioned within the outer holder 268, so as to cover the distal end 46 of the needle 38.

Figure 19:
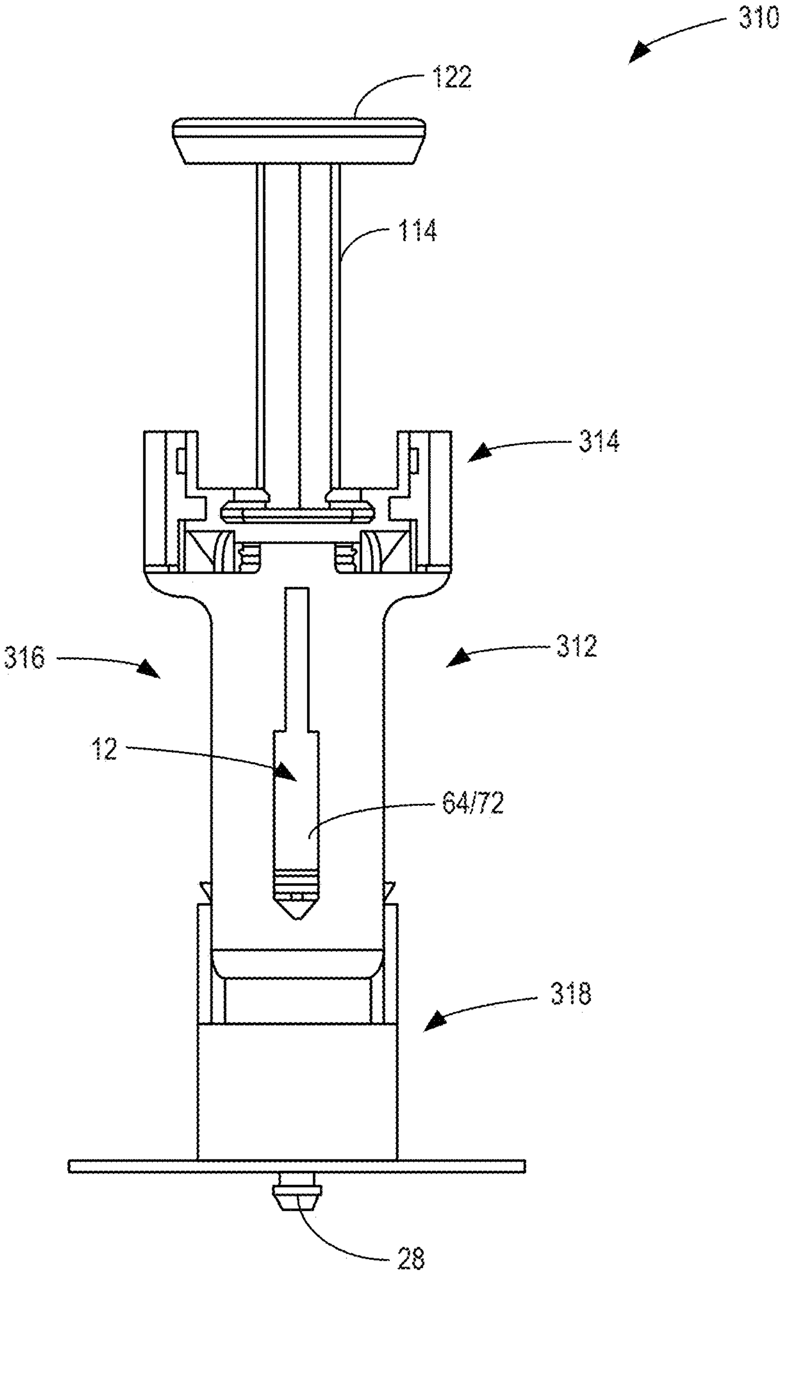
FIG. 19 is a perspective view of a 5-10 mL manual safety injector, according to another non-limiting embodiment described herein.

Referring now to FIGS. 19 and 20, shown is another non-limiting embodiment of a manually operated/activated safety injector 310 for injecting a 5-10 mL dosage of medicament into a patient. The safety injector 310 may be characterized as generally including a barrel or container assembly 12, an injector assembly 312, and a plunger (rod) 114 that may be pre-assembled by a manufacturer prior to receipt and use by a patient or other end user.

Regarding the container assembly 12, the container assembly 12 is structured identically to the container assembly 12 previously described in the safety injector of FIGS. 1-6. Accordingly, the container assembly 12 is not described in detail again herein but, as previously described, generally includes a container 18 (i.e., a cartridge or barrel) with a stopper 20 positioned and retained therein, a cap assembly 22 comprising a tip cap needle holder 24 and a protective cap 26, a needle cap 28, a septum 30, a pierceable membrane 32, and a needle assembly 34 comprising a hub 36 and a double-ended needle 38. The container 18 may be provided as a pre-filled cartridge or barrel that contains a volume of medicament or other fluid therein. As described above, the container 18 may contain a medicament or other fluid therein in the amount of 5-10 mL, such that the cartridge/barrel may be provided as a 5 mL cartridge/barrel, a 7 mL cartridge/barrel, or a 10 mL cartridge/barrel, as non-limiting examples.

The injector assembly 312 includes an inner container holder 314, a middle body 316, an outer holder 318, and a biasing member or spring 56.

The inner container holder 314 of the injector assembly 312 may comprise a generally elongated member that is configured to receive and retain the container assembly 12 therein. The inner container holder 314 may comprise a tube-shaped body 320 having an open proximal end 322 and an open distal end 324. The tube-shaped body 320 includes one or more windows 64 therein through which the container 18 may be viewed. The container assembly 12 may be introduced into the inner container holder 314 via the open proximal end 322, and may be advanced distally through the inner container holder 314 until a distal end of the container body 40 abuts a retainer (e.g., retaining clips or arms, extending radially inward from the tube-shaped body 320) formed at the distal end of the inner container holder 314. The cap assembly 22 and needle assembly 34 may then protrude distally out past the inner container holder 314.

The inner container holder 314 may further comprise a flanged lock member 326 at the proximal end of tube-shaped body 320. The lock member 326 is positioned at the open proximal end 322 of the tube-shaped body 320 and extends radially outward past the tube-shaped body 320. The lock member 326 defines a cavity 328 configured to receive a proximal lip of the container 18, as a well as a distal end of the plunger 114. The lock member 326 may include a pair of hook openings 330 therein that receive elements of the middle body 316 therein, as explained in further detail below. The lock member 326 may also include a lip 332 formed circumferentially thereabout that extends proximally and distally from the lock member 326.

The middle body 316 of the injector assembly 312 is positioned about the inner container holder 314 and receives inner container holder 314. The inner container holder 314 is received with the middle body 316 so as translatable therein in the longitudinal direction. The middle body 316 may generally comprise a sidewall structure 334, a proximal end member 336, and a distal end lip 338.

The sidewall structure 334 includes one or more windows 72 therein through which the container 18 may be viewed, with the window(s) 72 of the middle body 316 aligned with the window(s) 64 of the inner container holder 314. Additionally, a plurality of protrusions 340 may be formed on the sidewall structure 334, on an outer surface thereof and positioned near the distal end of the sidewall structure 334. The protrusions 340 are configured to have an angled distal-facing surface and a flat proximal-facing surface, to enable distal movement of the middle body 316 into the outer holder 318 but prohibit proximal movement of the middle body 316 out from the outer holder 318.

The proximal end member 336 of middle body 316 comprises a flared portion that extends radially outward from the sidewall structure 334. The proximal end member 336 includes a pair of hook members 342 that extend out in a proximal direction. The hook members 342 are aligned with the pair of hook openings 330 formed in the lock member 326 of inner container holder 314, with the hook members 342 configured to extend through the openings 330 and engage the lock member 326—thereby securing the middle body 316 to the inner container holder 314.

The distal end lip 338 of middle body 316 is formed internally within sidewall structure 334, with the lip 338 extending radially inward from an inner surface of the sidewall structure 334. The distal end lip 338 may function a holder or holding surface for the spring 56 of injector assembly 312, with the spring 56 seated between the distal end lip 338 and a proximal end of the container assembly 12 and/or inner container holder 314 (e.g., proximal end of the protective cap 26 and/or tube-shaped body 320).

The outer holder 318 of the injector assembly 312 has a tube-shaped holder body 344 sized to receive the middle body 316 therein. The holder body 344 is shorter in length than the middle body 316—with only a distal portion of the middle body 316 being received within the holder body 344. The holder body 344 includes a track 346 formed on each of opposing sides thereof that extends at least partially between a proximal end and distal end of the holder body 344—with the track 346 configured to engage with the protrusions 340 formed on the sidewall structure 334 of middle body 316. The track 346 interacts with the protrusions 340 to enable distal movement of the middle body 316 into the outer holder 318 but prohibit proximal movement of the middle body 316 out from the outer holder 318.

A foot 348 is provided on the outer holder 318 at the distal end of the holder body 344. The foot 348 may comprise a circular member that extends radially outward past the tube-shaped holder body 344. The foot 348 may substantially close the distal end of the holder body 344, but includes a needle opening 350 therein that accommodates positioning of the needle cap 28 therein, and allows for the needle 38 to extend/protrude therethrough when the middle body 316 is moved distally through the holder body 344, as explained in further detail below. A distal-facing surface of the foot 348 may comprise a generally flat surface and may be configured as a textured surface having a plurality of ribs—with the distal-facing surface configured to accommodate placement of the safety injector against the skin of a patient when in use.

The plunger comprises a plunger rod 114 that includes a main body extending between a plunger rod proximal end and a plunger rod distal end. A thumb press 122 is positioned at the plunger rod proximal end that may be engaged by a thumb (or other finger) of the user to apply a distally directed force to the plunger rod, to move the plunger rod 114 with respect to the container 18—i.e., advance the plunger rod (and stopper 20) distally into the container 18. In some embodiments, the thumb press 122 may have a concave profile and/or include ridges formed thereon, to improve engagement between a thumb and the thumb press. The plunger rod distal end is configured to mate with the stopper 20 positioned in container 18 and, in some embodiments, may include a flanged extension that engages a cavity formed in the stopper 20, and may also engage lock member 326 of inner container holder 314.

Referring now to FIGS. 20A-20D, operation of the safety injector 310 is described in more detail. As indicated above, the safety injector 310 is pre-assembled by a manufacture, so as to be provided to a user in a ready to use condition.

Figures 20A, 20B:
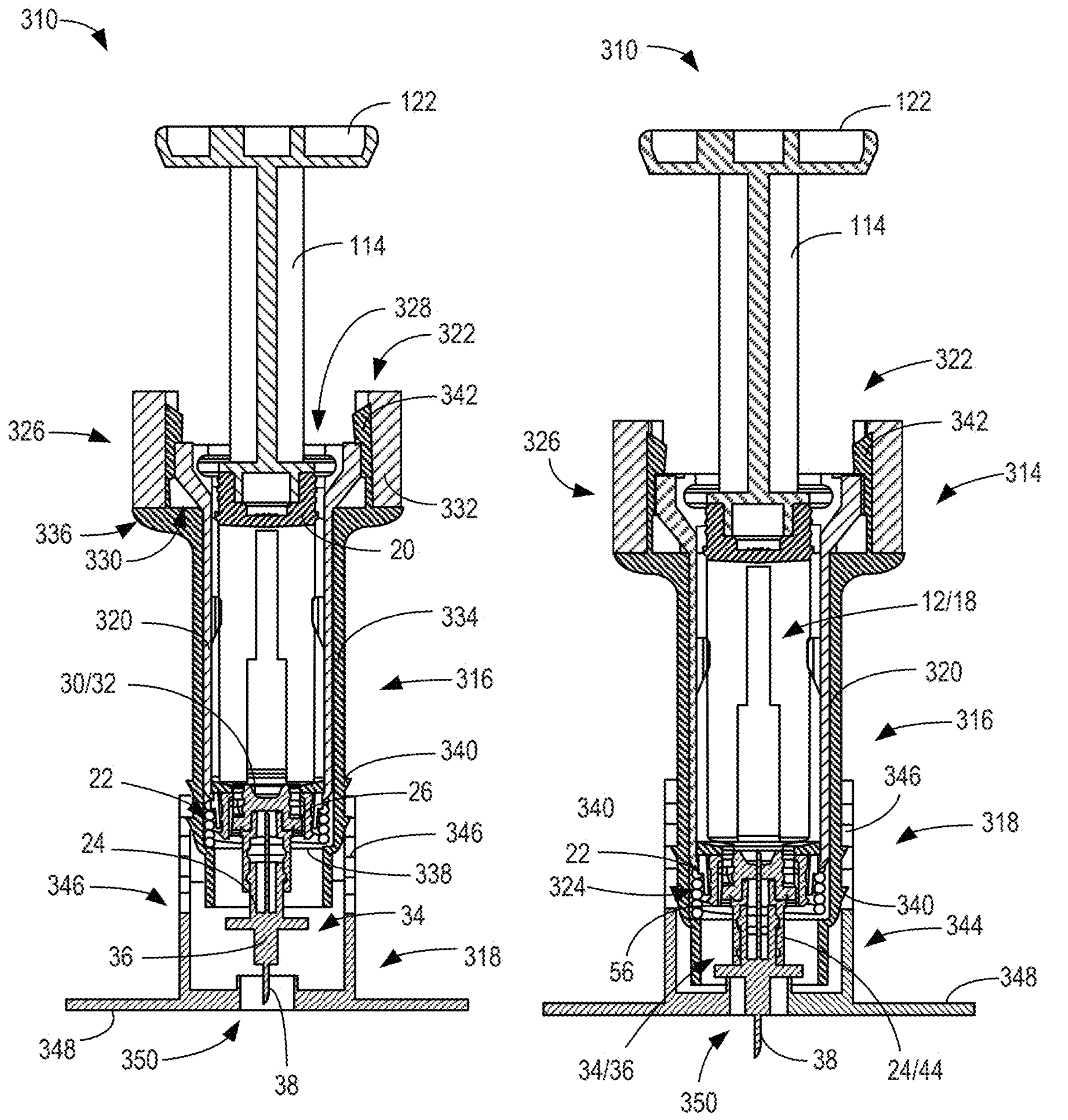
FIGS. 20A-20D are side cross-sectional views of the safety injector of FIG. 19, with the safety injector in different operational states.

From an initial configuration of the safety injector 310, as shown in FIG. 20A, a user will first remove the needle cap 28 (FIG. 19) from the injector.

With the needle cap 28 removed from the safety injector 310, the safety injector 310 may be applied to the skin of the patient, and the needle 38 may then be inserted into the patient, as shown in FIG. 20B. Insertion of the needle 38 is achieved by application of an initial, distally-directed pressure to the plunger rod 114, with this pressure causing the middle body 316 (and the inner container holder 314 and container assembly 12 retained therein) to move distally further into the holder body 344. Specifically, application of an initial, distally-directed pressure to the plunger rod 114 causes the protrusions 340 on middle body 316 to slide distally along track 346 on holder body 344, thereby providing for distal movement of the middle body 316 within the holder body 344. With the middle body 316 (and the inner container holder 314 and container assembly 12 retained therein) moved distally within the holder body 344, the needle 38 is caused to protrude out distally from the outer holder 318, such that the needle 38 is inserted into the patient with a controlled depth of penetration (i.e., the amount the needle extends out past outer holder 318/foot 348).

As part of the same initial, distally-directed pressure applied to the plunger rod 114, the needle assembly 34 may be caused to move proximally relative to cap assembly 22, in order to place the needle 38 in fluid communication with the container 18, as further shown in FIG. 20B That is, as the needle 38 is inserted into the patient during application of the initial, distally-directed pressure to the plunger rod 114, the hub 36 of needle assembly 34 comes into contact with the foot 348 of outer holder 318, such that the continued application of a distally-directed pressure to the plunger rod 114 causes the hub 36 to be pushed back proximally further into the annular seat 44 of the tip cap needle holder 24. As the hub 36 is pushed proximally back into the tip cap needle holder 24, the proximal end 45 of the needle 38 is caused to be driven through the septum 30, so as to place the needle 38 in fluid communication with the inner volume of container 18.

Figure 20C:
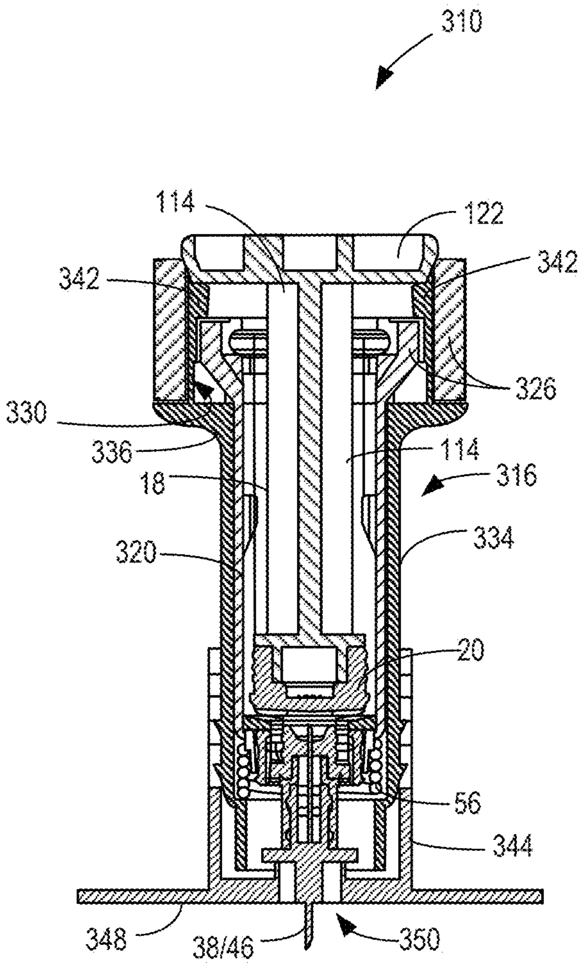

As shown in FIG. 20C, upon placing of the needle 38 in fluid communication with the container 18, a continued distally-directed pressure may be applied to the plunger rod 114 by a user, to force the medicament out from the container 18 and through the needle 38, for administering to the patient. That is, the user may continue to advance the plunger rod 114 and stopper 20 distally into the container 18, thereby forcing the medicament out from the container 18 and through the needle 38.

Figure 20D:
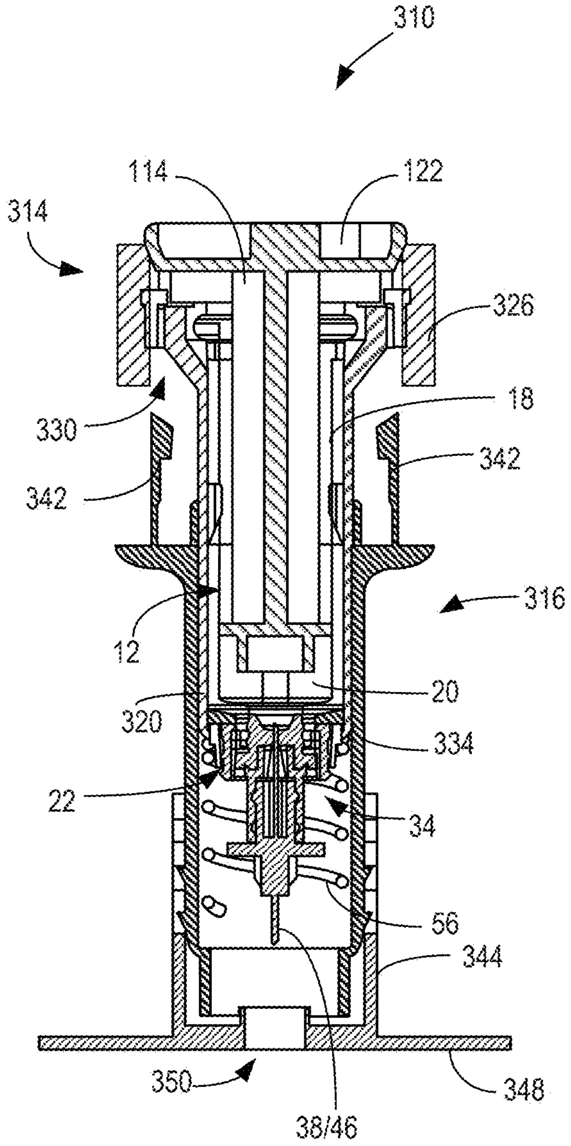

As the plunger rod 114 is approaching being fully depressed into the container 18, a distally-facing surface of the thumb press 122 of the plunger rod 114 is brought into contact with the pair of hook members 342 that extend out in a proximal direction from the proximal end member 336 of middle body 316. The thumb press 122 applies a distally directed force to the hook members 342, thereby causing the hook members 342 to become disengaged from the lock member 326 of inner container holder 314, such that the hook members 342 slide out through the pair of openings 330 formed in the lock member 326. With the hook members 342 forced out through the pair of openings 330, the inner container holder 314 is disengaged from middle body 316, thereby allowing for the spring 56 to be released and transition from its compressed state to its extended state. As the spring 56 transitions from its compressed state to its extended state, the inner container holder 314 is pushed back proximally within the middle body 316, as shown in FIG. 20D. With the inner container holder 314 moved back proximally within the middle body 316, the container assembly 12—and the needle assembly 34 thereof—is also caused to move back proximally, such that the needle 38 is retracted from the patient out through the needle opening 350 in foot 348, and back into the middle body 316 (and outer holder 318). With the container assembly 12 and needle assembly 34 retracted back proximally, the distal end 46 of the double-ended needle 38 is positioned within the middle body 316, so as to cover the distal end 46 of the needle 38.

Figure 21:
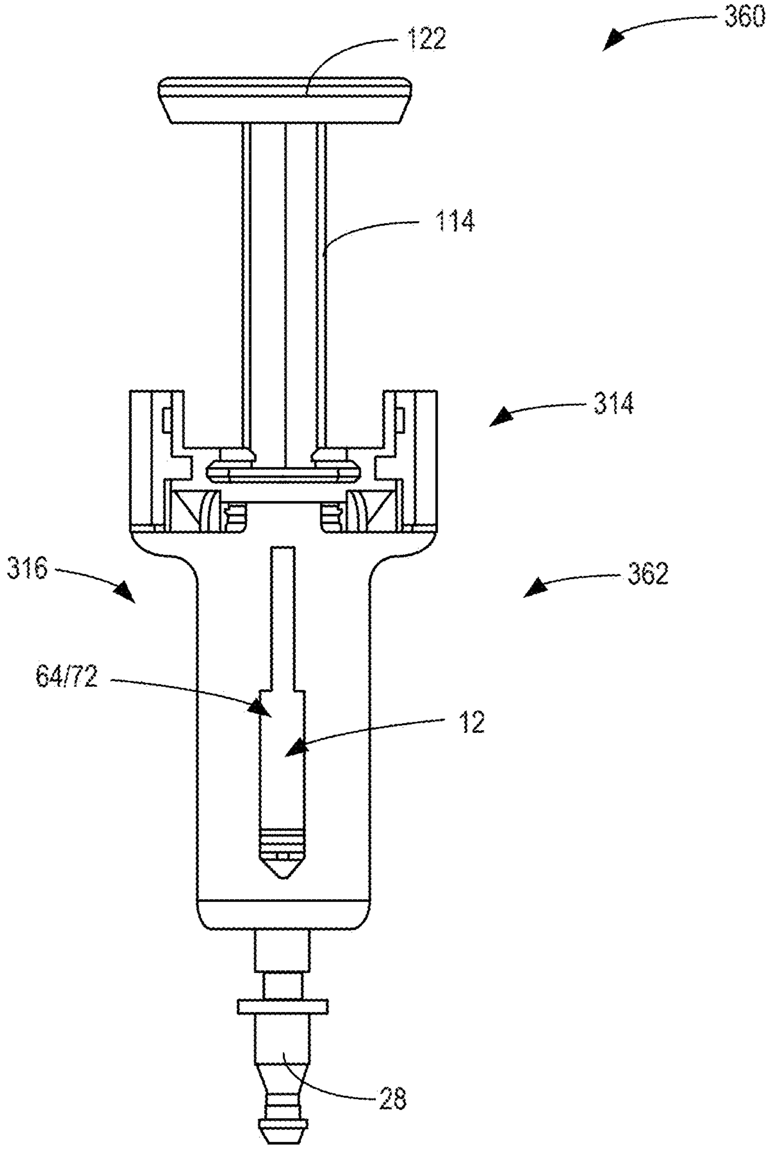
FIG. 21 is a perspective view of a 5-10 mL manual safety injector, according to another non-limiting embodiment described herein.

Referring now to FIGS. 21 and 22, shown is another non-limiting embodiment of a manually operated/activated safety injector 360 for injecting a 5-10 mL dosage of medicament into a patient. The safety injector 360 may be characterized as generally including a barrel or container assembly 12, an injector assembly 362, and a plunger (rod) 114, which all may be pre-assembled by a manufacturer prior to receipt and use by a patient or other end user.

Regarding the container assembly 12, the container assembly 12 is structured identically to the container assembly 12 previously described in the safety injector of FIGS. 1-6. Accordingly, the container assembly 12 is not described in detail again herein but, as previously described, generally includes a container 18 (i.e., cartridge or barrel) with a stopper 20 positioned and retained therein, a cap assembly 22 comprising a tip cap needle holder 24 and a protective cap 26, a needle cap 28, a septum 30, a pierceable membrane 32, and a needle assembly 34 comprising a hub 36 and a double-ended needle 38. The container 18 may be provided as a pre-filled cartridge or barrel that contains a volume of medicament or other fluid therein. As described above, the container 18 may contain a medicament or other fluid therein in the amount of 5-10 mL, such that the container 18 may be provided as a 5 mL cartridge/barrel, a 7 mL cartridge/barrel, or a 10 mL cartridge/barrel, as non-limiting examples.

The injector assembly 362 includes an inner container holder 314, a middle body 316, and a biasing member or spring 56. The inner container holder 314, middle body 316, and spring 56 are structured and arranged identical to the inner container holder 314, middle body 316, and spring 56 included in the safety injector of FIGS. 19 and 20 (except for protrusions 340 on the exterior of the middle body 316 being removed), and thus like numbering is used to indicate these components and the features thereon. As seen in FIGS. 21 and 22, the outer holder is eliminated from the safety injector 360.

Referring now to FIGS. 22A-22E, operation of the safety injector 360 is described in more detail. As indicated above, the safety injector 360 is pre-assembled by a manufacture, so as to be provided to a user in a ready to use condition.

From an initial configuration of the safety injector 360, as shown in FIG. 20A, a user first applies a proximally-directed force to the needle cap 28. Application of a proximally-directed force to the needle cap 28 causes the needle assembly 34 to move proximally relative to the cap assembly 22 of container assembly 12, in order to place the needle 38 in fluid communication with the container 18. That is, as a proximally-directed force is applied to the needle cap 28, the hub 36 of needle assembly 34 is caused to be pushed back proximally further into the annular seat 44 of the tip cap needle holder 24. As the hub 36 is pushed proximally back into the tip cap needle holder 24, the proximal end 45 of the needle 38 is caused to be driven through the septum 30, so as to place the needle 38 in fluid communication with the inner volume of container 18.

Figure 22A:
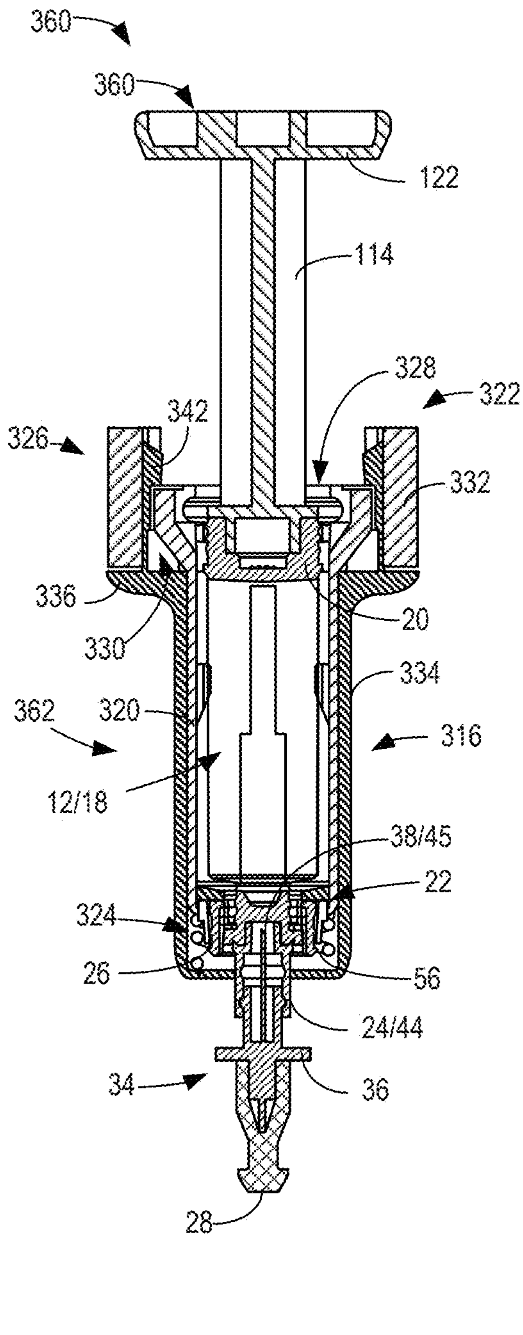
FIGS. 22A-22E are side cross-sectional views of the safety injector of FIG. 21, with the safety injector in different operational states.
Figure 22B:
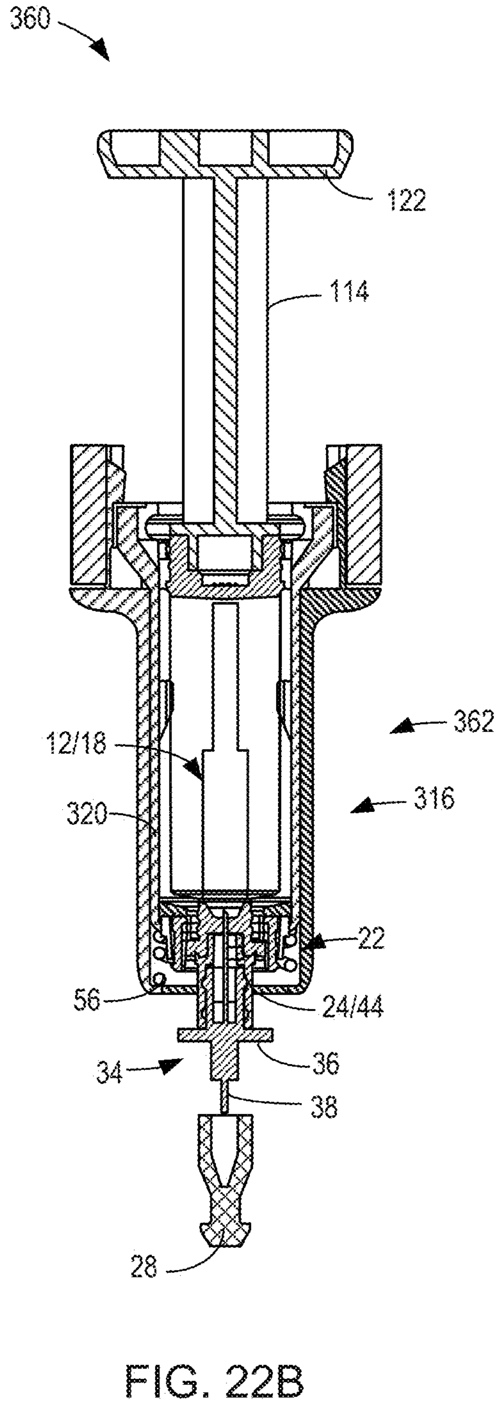

With the needle 38 placed in fluid communication with the container 18, a user then removes the needle cap 28 from the safety injector 360 to prepare the injector for a subsequent injection, as shown in FIG. 22B.

Figure 22C:
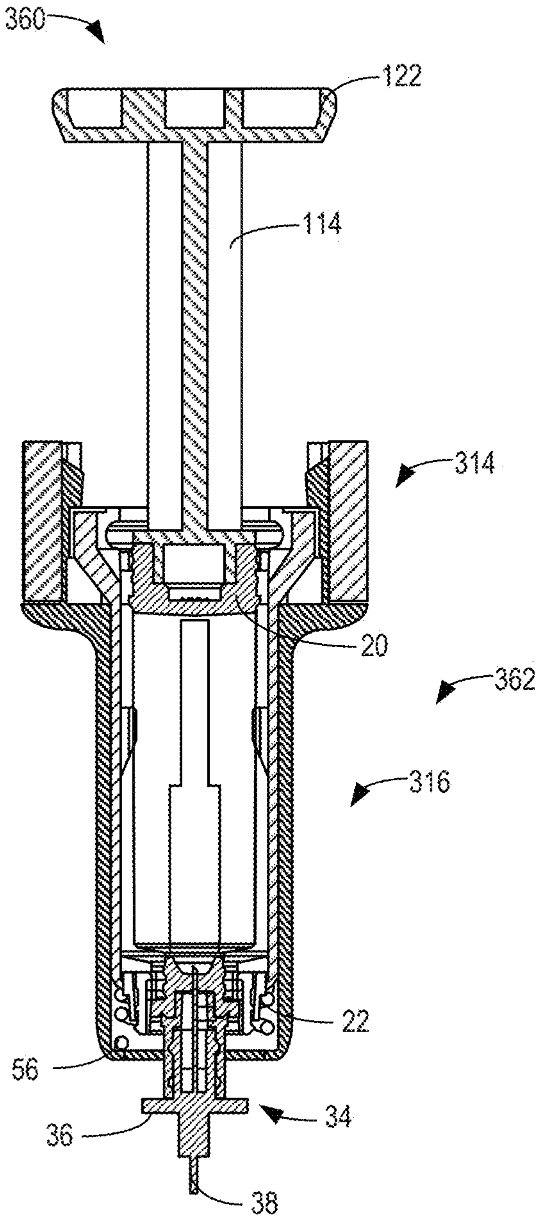

With the needle cap 28 removed from the safety injector 360, the needle 38 may then be inserted into the patient, as shown in FIG. 22C.

Figure 22D:
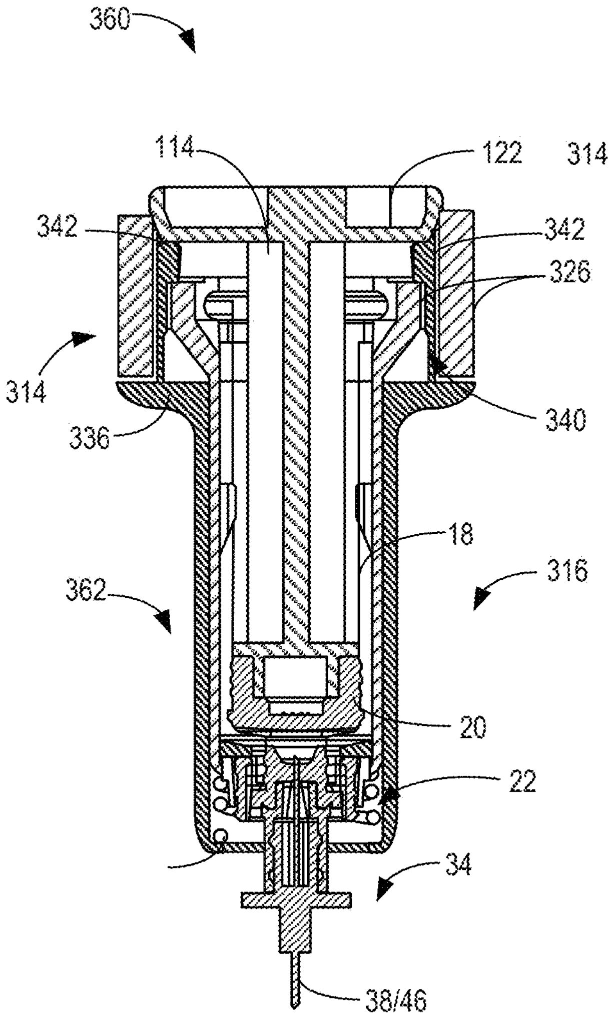

As shown in FIG. 22D, upon insertion of the needle 38 into the patient, a distally-directed pressure may be applied to the plunger rod 114 by a user, to force the medicament out from the container 18 and through the needle 38, for administering to the patient. That is, the user may advance the plunger rod 114 and stopper 20 distally into the container 18, thereby forcing the medicament out from the container 18 and through the needle 38.

Figure 22E:
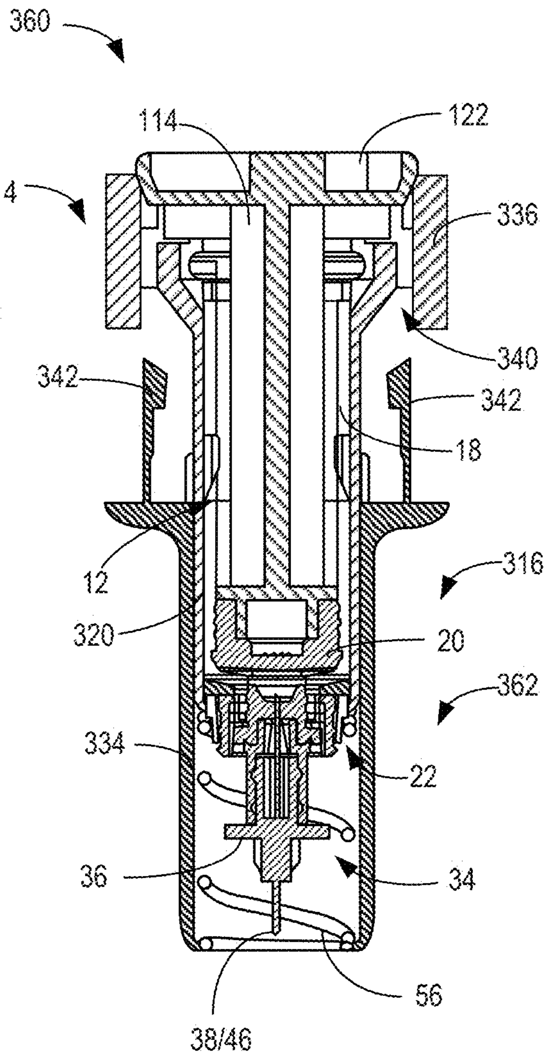

As the plunger rod 114 is approaching being fully depressed into the container 18, a distally-facing surface of the thumb press 122 of the plunger rod 114 is brought into contact with the pair of hook members 342 that extend out in a proximal direction from the proximal end member 336 of middle body 316. The thumb press 122 applies a distally directed force to the hook members 342, thereby causing the hook members 342 to become disengaged from the lock member 326 of inner container holder 314, such that the hook members 342 slide out through the pair of openings 330 formed in the lock member 326. With the hook members 342 forced out through the pair of openings 330, the inner container holder 314 is disengaged from middle body 316, thereby allowing for the spring 56 to be released and transition from its compressed state to its extended state. As the spring 56 transitions from its compressed state to its extended state, the inner container holder 314 is pushed back proximally within the middle body 316, as shown in FIG. 22E. With the inner container holder 314 moved back proximally within the middle body 316, the container assembly 12—and the needle assembly 34 thereof—is also caused to move back proximally, such that the needle 38 is retracted from the patient and back into the middle body 316. With the container assembly 12 and needle assembly 34 retracted back proximally, the distal end 46 of the double-ended needle 38 is positioned within the middle body 316, so as to cover the distal end 46 of the needle 38.

Although the present disclosure has been described in detail for the purpose of illustration based on what is currently considered to be the most practical and preferred embodiments or aspects, it is to be understood that such detail is solely for that purpose and that the present disclosure is not limited to the disclosed embodiments or aspects, but, on the contrary, is intended to cover modifications and equivalent arrangements that are within the spirit and scope of the appended claims. For example, it is to be understood that the present disclosure contemplates that, to the extent possible, one or more features of any embodiment may be combined with one or more features of any other embodiment.

The invention claimed is:

1. A manual safety injector comprising:
- a container assembly comprising:
  - a container pre-filled with 5 to 10 mL of fluid therein, with a stopper positioned in the container at a proximal end thereof and a septum positioned in the container at a distal end thereof, to seal the fluid in the container; and
  - a needle assembly comprising a double-ended needle having a sharp proximal end and a sharp distal end;
- an injector assembly comprising:
  - an inner container holder within which the container is retained;
  - a middle body positioned about the inner container holder, with the inner container holder movable within the middle body in a longitudinal direction;
  - an outer holder positioned about the middle body, with the middle body movable within the outer holder in a longitudinal direction; and
  - a biasing member positioned between the middle body and the outer holder, at a distal end of each of the middle body and the outer holder; and
- a plunger assembly engageable with the injector assembly and the container assembly and including a plunger rod or shaft configured to advance the stopper within the container to expel fluid out from the container;
- wherein a first actuation of the plunger assembly causes the inner container holder to move distally within the middle body, to extend the sharp distal end of the needle out distally past the outer holder for insertion of the needle into a patient, and causes the needle assembly to move from a first position where the sharp proximal end is separated from the septum to a second position where the sharp proximal end is positioned to pierce through the septum, to place the needle in fluid communication with the fluid within the container; and
- wherein an additional actuation of the plunger assembly causes the fluid to be expelled out from the container and causes the middle body to release from the outer holder, such that the biasing member is able to actuate and move the container assembly, the inner container holder, and the middle body distally within the outer holder, to retract the sharp distal end of the needle back into the outer holder.

2. The manual safety injector of claim 1, further comprising a cap assembly positioned at the distal end of the container, the cap assembly comprising:
- a protective cap engaged to a port of the container, at the distal end of the container; and
- a tip cap needle holder engaged with the protective cap, the tip cap needle holder including an annular seat configured to receive a portion of the needle assembly.

3. The manual safety injector of claim 2, wherein the needle assembly comprises a hub comprising a distal end, a proximal end, with a hole extending between the distal and proximal ends of the hub that retains the needle therein, and wherein the proximal end of the hub is seated within the annular seat of the tip cap needle holder and is seated therein.

4. The manual safety injector of claim 3, wherein the hub moves proximally into the annular seat upon application of a sufficient force against the hub, thereby moving the needle assembly from the first position to the second position, so that the sharp proximal end pierces through the septum, to place the needle in fluid communication with the fluid within the container.

5. The manual safety injector of claim 3, wherein the needle assembly comprises a needle cap coupled to the distal end of the hub, so as to be positioned over the sharp distal end of the needle.

6. The manual safety injector of claim 3, wherein the outer holder comprises a foot at the distal end thereof that substantially closes the distal end of the outer holder, the foot comprising a flat distal-facing surface configured for placement against the skin of a patient during use of the manual safety injector.

7. The manual safety injector of claim 6, wherein the distal-facing surface of the foot comprises an adhesive patch that covers a portion or all of the distal-facing surface.

8. The manual safety injector of claim 6, wherein the injector assembly further comprises a safety cap affixed to the distal-facing surface of the foot, the safety cap comprising:

a cover applied over the distal-facing surface of the foot, the cover including a needle opening therein;

a pull tab extending over distally from the cover and including a grip configured to be pulled by a user; and a loop connecting the pull tab and the cover, so that a pulling force applied to the grip is transferred to the cover, to enable removal of the safety cap from the foot.

9. The manual safety injector of claim 8, wherein the safety cap comprises a receptacle therein extending proximally through the cover, the receptacle configured to receive and retain the needle cap therein, such that removal of the safety cap from the foot also causes removal of the needle cap.

10. The manual safety injector of claim 1, wherein the middle body comprises a proximal end member including a flanged portion having a pair of openings formed therein, and wherein the outer holder comprises a pair of hook members formed at a proximal end thereof and that extend out in a proximal direction through the pair of openings to engage the proximal end member.

11. The manual safety injector of claim 10, wherein the plunger assembly comprises:

a plunger rod and a thumb press at a proximal end of the plunger rod; and a plunger retainer positioned on the plunger rod, with an opening formed through the plunger retainer through which the plunger rod extends, the plunger retainer configured to engage the inner container holder.

12. The manual safety injector of claim 11, wherein the additional actuation of the plunger assembly causes the thumb press to push distally against the pair of hook members and cause the pair of hook members to disengage from the proximal end member and slide distally through the pair of openings, thereby releasing the middle body from the outer holder.

13. The manual safety injector of claim 11, wherein the plunger assembly comprises:

an outer grip having a closed proximal end and an open distal end, with an inner surface of the outer grip defining a hollow inner chamber; and a plunger shaft connected to the inner surface at the closed proximal end and extending distally therefrom, the plunger shaft configured to engage the stopper and advance the stopper distally within the container.

14. The manual safety injector of claim 13, wherein the outer grip comprises a pair of longitudinally oriented rails formed on opposing sides of the inner surface the pair or rails configured to interact with the middle body and outer holder, to provide for a distal advancement of the plunger assembly.

15. The manual safety injector of claim 14, wherein the middle body further comprises a pair of release tabs configured to selectively engage the outer holder to retain the middle body in-place within the outer holder, and wherein the additional actuation of the plunger assembly causes the pair of rails to deflect the pair of release tabs, thereby releasing the middle body from the outer holder.

16. The manual safety injector of claim 6, further comprising a skin sensor retained by the middle body and the outer holder, the skin sensor moveable between a first position where the skin sensor extends out distally past the foot of the outer holder and a second position where the skin sensor does not extend out distally past the foot of the outer holder.

17. The manual safety injector of any claim 16, wherein the skin sensor comprises a U-shaped slide member including:

a cross-bracket having a first end and a second end;

a first sliding guide positioned at the first end of the cross-bracket and extending proximally from the cross-bracket; and a second sliding guide positioned at the second end of the cross-bracket and extending proximally from the cross-bracket;

wherein the first and second sliding arms slide proximally within guide grooves on the middle body to move the skin sensor from the first position to the second position.

18. The manual safety injector of claim 17, wherein the injector assembly further comprises a safety cap affixed to the distal-facing surface of the foot, the safety cap comprising:

a cover applied over the distal-facing surface of the foot, the cover including a needle opening and a pair of arm openings therein, the first and second sliding arms extending through the arm openings;

a pull tab extending over distally from the cover and including a grip configured to be pulled by a user; and a pair of concentric receptacles formed in a portion of the cover, the pair of receptacles including:

a first larger receptacle sized and arranged to accommodate a portion of the skin sensor therein when the skin sensor is in the first position; and a second receptacle positioned within the first receptacle and sized and arranged to receive the needle cap therein.

19. The manual safety injector of claim 18, wherein the distal-facing surface of the foot further comprises a depression formed therein configured to receive the cross-bracket when the skin sensor is in the second position.

20. The manual safety injector of claim 1, wherein each of the inner container holder, the middle body, and the outer holder includes one or more windows therein that enable viewing of the container and a position of the stopper.

21. The manual safety injector of claim 1, wherein after the additional actuation of the plunger assembly, the plunger assembly is locked in position by the injector assembly.

22. The manual safety injector of claim 1, wherein the biasing member comprises a spring configured to transition from a compressed state to an extended state, the spring transitioning from the compressed state to the extended state to move the container assembly, the inner container holder, and the middle body distally within the outer holder, and thereby retract the sharp distal end of the needle back into the outer holder.

* * * * *